United States Patent
Zhong et al.

(10) Patent No.: US 9,718,770 B2
(45) Date of Patent: Aug. 1, 2017

(54) SUBSTITUTED THIOUREAS AS HEAT SHOCK PROTEIN 70 INHIBITORS

(71) Applicant: Institute of Pharmacology and Toxicology Academy of Military Medical Sciences P.L.A. China, Beijing (CN)

(72) Inventors: Wu Zhong, Beijing (CN); Song Li, Beijing (CN); Yanqun Zeng, Beijing (CN); Junhai Xiao, Beijing (CN); Xinbo Zhou, Beijing (CN); Zhibing Zheng, Beijing (CN); Xingzhou Li, Beijing (CN); Xiaokui Wang, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 15/105,426

(22) PCT Filed: Dec. 18, 2014

(86) PCT No.: PCT/CN2014/094162
§ 371 (c)(1),
(2) Date: Jun. 16, 2016

(87) PCT Pub. No.: WO2015/090209
PCT Pub. Date: Jun. 25, 2015

(65) Prior Publication Data
US 2016/0311767 A1    Oct. 27, 2016

(30) Foreign Application Priority Data
Dec. 20, 2013   (CN) .......................... 2013 1 0704756

(51) Int. Cl.
| | | |
|---|---|---|
| *A61K 31/155* | (2006.01) | |
| *A61K 31/17* | (2006.01) | |
| *C07C 335/04* | (2006.01) | |
| *C07C 391/00* | (2006.01) | |
| *C07D 213/75* | (2006.01) | |
| *C07C 335/08* | (2006.01) | |
| *C07C 335/14* | (2006.01) | |
| *C07C 335/16* | (2006.01) | |
| *C07C 335/18* | (2006.01) | |
| *C07D 295/16* | (2006.01) | |
| *C07C 335/20* | (2006.01) | |
| *C07D 211/06* | (2006.01) | |

(52) U.S. Cl.
CPC .......... *C07C 391/00* (2013.01); *C07C 335/08* (2013.01); *C07C 335/14* (2013.01); *C07C 335/16* (2013.01); *C07C 335/18* (2013.01); *C07C 335/20* (2013.01); *C07D 211/06* (2013.01); *C07D 213/75* (2013.01); *C07D 295/16* (2013.01); *C07C 2101/02* (2013.01); *C07C 2101/14* (2013.01); *C07C 2101/16* (2013.01)

(58) Field of Classification Search
CPC ..... A61K 31/155; A61K 31/17; C07C 335/04
USPC .............................. 514/579; 564/17
See application file for complete search history.

(56) References Cited

U.S. PATENT DOCUMENTS

| 6,645,968 B2 | 11/2003 | Altenbach et al. |
| 2004/0171073 A1 | 9/2004 | Neiland et al. |

FOREIGN PATENT DOCUMENTS

| CN | 101489542 A | 7/2009 |
| CN | 102028689 A | 4/2011 |
| CN | 102241628 A | 11/2011 |
| CN | 102241673 A | 11/2011 |
| EP | 1 832 283 A1 | 9/2007 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — Sterne, Kessler, Goldstein & Fox P.L.L.C.

(57) ABSTRACT

The invention provides a compound of Formula I, an isomer, a pharmaceutically acceptable salt, or a solvate thereof, and use thereof in manufacture of a medicament for preventing and/or treating a drug-resistant tumor or disease or disorder caused by a drug-resistant bacterium, or use thereof in manufacture of a medicament for preventing and/or treating a tumor, a neurodegenerative disease, an allogeneic graft rejection, or an infection-associated disease or disorder; preferably, the tumor, neurodegenerative disease, allogeneic graft rejection, or infection-associated disease or disorder is a disease or disorder caused by Heat shock protein 70 (Hsp70). The compounds of the invention, which are a class of Hsp70 inhibitors having a novel structure and a high activity, solve the problem concerning drug resistance of tumors, enhance the effect of treating tumors, and provide a new medical strategy for treatment of tumors in clinic.

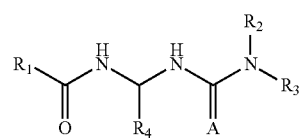

I

25 Claims, 1 Drawing Sheet

(56) References Cited

FOREIGN PATENT DOCUMENTS

| WO | WO 02/22581 A1 | 3/2002 |
|---|---|---|
| WO | WO 2004/032716 A2 | 4/2004 |
| WO | WO 2005/033288 A2 | 4/2005 |
| WO | WO 2006/110724 A2 | 10/2006 |
| WO | WO 2007/015632 A1 | 2/2007 |
| WO | WO 2007/101710 A1 | 9/2007 |
| WO | WO 2008/066576 A2 | 6/2008 |
| WO | WO 2008/066576 A3 | 6/2008 |

OTHER PUBLICATIONS

Vippagunta, et al. Advanced Drug Delivery Reviews, 48, 2001, 18.*
Long, et al. Bioorganic & Medicinal Chemistry Letters, 15(17), 2005, 3849-3852.*
International Search Report (ISR) for PCT/CN2014/094162; I.A. fd: Dec. 18, 2014, mailed Mar. 24, 2015, State Intellectual Property Office of the P.R. China, Beijing, China.
International Preliminary Report on Patentability (IPRP) including the Written Opinion of the International Searching Authority (PCT Rule 44bis) for PCT/CN2014/094162; I.A. fd: Dec. 18, 2014, issued Jun. 21, 2016, by the International Bureau of WIPO, Geneva, Switzerland.
Extended European search report, including the supplementary European search report and the European search opinion, for EP Appl. No. 14871208.6, dated May 4, 2017, European Patent Office, Munich, Germany.
Perola, E. et aL, "Successful virtual screening of a chemical database for farnesyltransferase inhibitor leads," J Med Chem. 2000 Feb 10,43(3):401-8, American Chemical Society, Washington, DC.
Perez-Medrano, a. et al., "Design and synthesis of novel cyanoguanidine ATP-sensitive potassium channel openers for the treatment of overactive bladder," Bioorg Med Chem Lett. 2004 Jan 19;14(2):397-400, Elsevier, Oxford, England.
Taldone, T. et al., "Protein chaperones: a composition of matter review (2008 - 2013)," Expert Opin Ther Pat. May 2014;24(5):501-18. doi: 10.1517/13543776.2014.887681, Informa Healthcare, London, England.

* cited by examiner

SUBSTITUTED THIOUREAS AS HEAT SHOCK PROTEIN 70 INHIBITORS

CROSS-REFERENCE TO RELATED APPLICATIONS

None

STATEMENT REGARDING FEDERALLY SPONSORED RESEARCH OR DEVELOPMENT

None

THE NAMES OF THE PARTIES TO A JOINT RESEARCH AGREEMENT

None

INCORPORATION-BY-REFERENCE OF MATERIAL SUBMITTED ON A COMPACT DISC

None

BACKGROUND OF THE INVENTION

Field of the Invention

The invention relates to medical field, particularly novel urea compounds, preparation methods and uses thereof.

Description of Related Art

Heat shock protein 70 (Hsp70), which is widely present in nucleus, cytoplasm, endoplasmic reticulum, mitochondrion, and chloroplast cell, is involved in denovo synthesis, localization, maturation of proteins and degradation of misfolded proteins in cells, thereby affecting the growth and metabolic functions of cells. In cells, the binding of Hsp70 to nascent polypeptide on ribosomes can prevent misfolding of nascent polypeptides; Hsp70 is essential for the remodeling of clathrin during pinocytosis in mammalian cells; the binding of Hsp70 to protein in a non-natural conformation can promote the correct folding and assembly of protein, maintain the extended conformation of protein precursor and prevent aggregation, denaturation and degradation thereof, thereby facilitating the transport to organelles thereof.

Studies show that Hsp70 is associated with many diseases such as cancer, neurodegenerative disease, allogeneic graft rejection, and infection. In tumor cells, Hsp70 affects apoptosis mainly by the following pathways:

(1) Mitochondrial Pathway, wherein in early stage of mitochondrion, Hsp70 inhibits the release of cytc and AIF from mitochondrion by blocking the migration of Bax and reducing the permeability of mitochondrial outer membrane; in late stage of mitochondria, Hsp70 binds to Apaf1 directly, and suppress the aggregation of procaspase-9, which causes that apoptotic bodies cannot be formed and downstream caspase-3 cannot be activated;

(2) Death receptor pathway, wherein Hsp70 binds to Akt and PKC by inhibiting the activation of JNK, which causes that kinases are dephosphorylated, proteins are stabilized, and cells survive; similarly, Hsp70 can also bind to DR4 and DR5 to inhibit aggregation and activity of DISC induced by TRAIL;

(3) DNA degradation pathway, wherein Hsp70, Hsp40, and ICAD complex can inhibit the activity and folding effect of DNase CAD so that chromosome DNA in late apoptosis cannot be degraded, thereby achieving the anti-apoptotic effect.

Research on use of Hsp70 in tumor treatment has become a hot spot in recent years, however, inhibitors with a high activity have not been found yet, and the mechanism of action thereof is not clear yet. In tumor cells, the expression of Hsp70 and relevant proteins thereof is increased abnormally. Experiments demonstrate that after stimulation by administration of a drug, tumor cells exert potential defensing mechanism by virtue of Hsp70, and generate the drug resistance, resulting in the reduced drug activity. Hsp70 inhibitors are prospective in reversing the resistance of tumor cells to an anti-tumor drug.

BRIEF SUMMARY OF THE INVENTION

The inventor of the invention designed and synthesized a series of compounds with novel structures, which were found in experiments to be capable of inhibiting the growth of tumor cells as Hsp70 inhibitors, and capable of effectively reversing the drug-resistance of tumor cells. The invention is accomplished based on the above discovery.

DETAILED DESCRIPTION OF THE INVENTION

Figure 1:
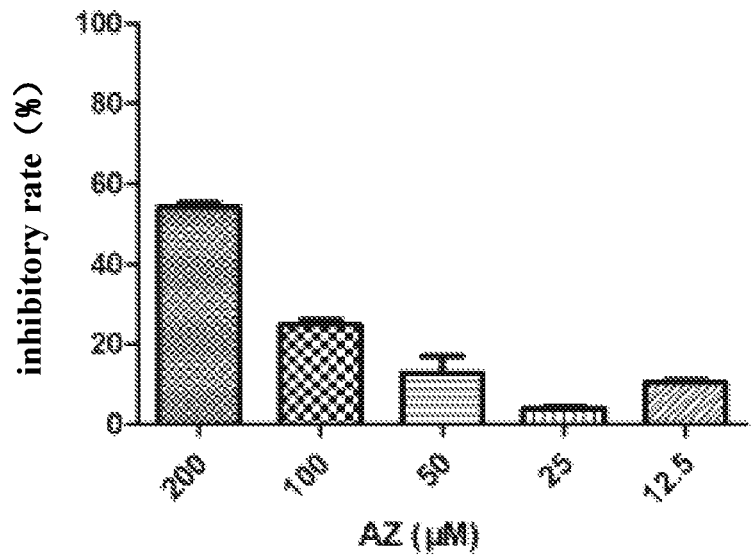
FIG. 1 illustrates the dose-response relationship with respect to the inhibition of Hsp70 ATPase enzymatic activity by positive control drug AZ.

In a first aspect, the invention relates to a compound of Formula I, an isomer, a pharmaceutically acceptable salt or a solvate thereof,

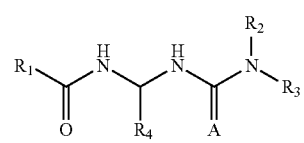

wherein:

A represents S or Se;

$R_1$ represents alkyl, substituted alkyl, cycloalkyl, substituted cycloalkyl, aryl, substituted aryl, aryl alkyl, substituted aryl alkyl, aryl alkenyl, substituted aryl alkenyl, heterocyclyl, substituted heterocyclyl, heterocyclyl alkyl or substituted heterocyclyl alkyl;

$R_2$ and $R_3$ each independently represent hydrogen, alkyl, cycloalkyl, substituted cycloalkyl, alkoxyalkyl, aminoalkyl, monosubstituted or disubstituted aminoalkyl, aromatic heterocyclyl, substituted aromatic heterocyclyl, arylalkyl, substituted arylalkyl, heterocyclyl alkyl, substituted heterocyclyl alkyl, aromatic heterocyclyl alkyl, substituted aromatic heterocyclyl alkyl, aryl, substituted aryl, heterocyclyl, substituted heterocyclyl, wherein $R_2$ and $R_3$ together can optionally form a ring;

$R_4$ represents hydrogen, haloalkyl, aliphatic group, wherein the aliphatic group is selected from alkyl, cycloalkyl, alkenyl, alkenylalkyl, alkoxyalkyl, alkoxycarbonyl, alkynyl.

In one embodiment of the invention, the haloalkyl in $R_4$ is selected from $CF_3$, $CCl_3$, $CBr_3$, and $CI_3$.

In one embodiment of the invention, the alkyl in $R_4$ is selected from methyl, ethyl, propyl, cyclopropyl, neopentyl, tert-pentyl, tert-butyl, and isobutyl.

The compound of Formula I, an isomer, a pharmaceutically acceptable salt, or a solvate thereof according to the first aspect of the invention, wherein, A represents Se or S;

$R_1$ is selected from cycloalkyl having 3-10 carbon atoms, arylalkenyl or substituted arylalkenyl, wherein the alkenyl comprises one or two or more carbon-carbon double bond, and the alkenyl and the aryl form a conjugated system; wherein the cycloalkyl or aryl is optionally substituted by one or more of the following groups $C_{1-6}$ alkyl, $C_{1-6}$ alkoxyl, cyano, halogen, hydroxyl, amino, nitro, mono-$C_{1-6}$alkyl amino, di-$C_{1-6}$alkyl amino, $C_{2-6}$ alkenyl, $C_{2-6}$ alkynyl, $C_{1-6}$ haloalkyl or $C_{1-6}$ haloalkoxyl;

$R_2$ and $R_3$ each independently are selected from hydrogen; $C_{1-10}$ alkyl, preferably $C_{1-6}$ alkyl; $C_{1-6}$ alkoxyl-$C_{1-6}$ alkyl; $C_{1-6}$ aminoalkyl; $C_{1-6}$-monosubstituted or disubstituted aminoalkyl; cycloalkyl having 3-10 carbon atoms; aryl or substituted aryl; aromatic heterocyclyl or substituted aromatic heterocyclyl; aryl alkyl or substituted aryl alkyl; wherein $R_2$ and $R_3$ together can optionally form a 3-8 membered ring containing C, N, O or S; the aryl is selected from phenyl, naphthyl, 1,2,3,4-tetrahydronaphthyl and indenyl; the aromatic heterocyclyl comprises a monocyclic or bicyclic 5-10 membered aromatic ring substituted by at least one heteroatom independently selected from N, O or S; $R_2$ or $R_3$ is optionally substituted by one or more of the following groups: $C_{1-6}$ alkyl, $C_{1-6}$ alkoxyl, cyano, halogen, hydroxyl, amino, nitro, mono-$C_{1-6}$alkyl amino, di-$C_{1-6}$alkyl amino, $C_{2-6}$ alkenyl, $C_{2-6}$ alkynyl, $C_{1-6}$ haloalkyl or $C_{1-6}$ haloalkoxyl;

$R_4$ is selected from trihalomethyl, $C_{1-10}$ alkyl and $C_{3-8}$ cycloalkyl.

The compound of Formula I, an isomer, a pharmaceutically acceptable salt, or a solvate thereof according to the first aspect of the invention, wherein, A represents Se or S;

$R_1$ represents cycloalkyl, styryl, substituted styryl;

$R_2$ and $R_3$ each independently represent hydrogen, methyl, propyl, butyl, isobutyl, 2-methoxyethyl, 3-isopropoxy propyl, 2-N,N-dimethylethyl, cyclohexyl, cycloheptyl, phenyl, 2-methoxyphenyl, 4-methoxyphenyl, 4-fluorophenyl, 2-chlorophenyl, 4-chlorophenyl, 2-bromophenyl, 3-bromophenyl, 4-bromophenyl, 2-methylphenyl, 2,3-dimethylphenyl, benzyl, 2-chlorobenzyl, 3-nitrophenyl, 2,4-difluorophenyl, 3-chloro-2-methylphenyl, 2,3-dichlorophenyl, 4-hydroxyphenyl, 2-pyridyl, 3-pyridyl, 4-pyridyl, wherein $R_2$ and $R_3$ together can optionally form a piperidine ring, a morpholine ring, or an N-methyl piperazine ring;

$R_4$ represents $CF_3$, $CCl_3$, $CBr_3$, $CI_3$, cyclopropyl, propyl, isopropyl, neopentyl, tert-pentyl, tert-butyl, isobutyl, 3,3-dimethylbutyl.

The compound of Formula I, an isomer, a pharmaceutically acceptable salt, or a solvate thereof according to the first aspect of the invention, wherein, A represents Se or S;

$R_1$ represents cyclopropyl, styryl, 3,4,5-methoxystyryl;

$R_2$ and $R_3$ each independently represent hydrogen, methyl, propyl, butyl, isobutyl, 2-methoxyethyl, 3-isopropoxy propyl, 2-N,N-dimethylethyl, cyclohexyl, cycloheptyl, phenyl, 2-methylphenyl, 2-methoxyphenyl, 4-methoxyphenyl, 4-fluorophenyl, 2-chlorophenyl, 4-chlorophenyl, 2-bromophenyl, 3-bromophenyl, 4-bromophenyl, 2,3-dimethylphenyl, benzyl, 2-chlorobenzyl, 3-nitrophenyl, 2,4-difluorophenyl, 3-chloro-2-methylphenyl, 2,3-dichlorophenyl, 4-hydroxyphenyl, 2-pyridyl, 3-pyridyl, 4-pyridyl, wherein $R_2$ and $R_3$ together can optionally form a piperidine ring, a morpholine ring, or an N-methyl piperazine ring;

$R_4$ represents $CF_3$, $CCl_3$, $CBr_3$, $CI_3$, cyclopropyl, propyl, isopropyl, neopentyl, tert-pentyl, tert-butyl, isobutyl, 3,3-dimethylbutyl.

The compound of Formula I, an isomer, a pharmaceutically acceptable salt, or a solvate thereof according to the first aspect of the invention is selected from the following compounds:

(1) (2E)-N-{2,2,2-trichloro-1-[3-(4-chlorophenyl) selenourea]-ethyl}-cinnamamide;
(2) (2E)-N-{2,2,2-trichloro-1-[3-(2-methoxyphenyl)selenourea]-ethyl}-cinnamamide;
(3) (2E)-N-{2,2,2-trichloro-1-[3-(2-methoxyphenyl)selenourea]-ethyl}-cyclopropyl formamide;
(4) (2E)-N-{2,2,2-trichloro-1-[(morpholin-4-selenoformyl)amino]-ethyl} cinnamamide;
(5) (2E)-N-{2,2,2-trichloro-1-[3-(3-nitrophenyl) selenourea]-ethyl} cinnamamide;
(6) (2E)-N-{2,2,2-trichloro-1-[3-(2,4-difluorophenyl)selenourea]-ethyl} cinnamamide;
(7) (2E)-N-{2,2,2-trichloro-1-[(piperidin-1-selenoformyl)amino]-ethyl} cinnamamide;
(8) (2E)-N-{2,2,2-trichloro-1-[3-(4-fluorophenyl) selenourea]-ethyl} cinnamamide;
(9) (2E)-N-[2,2,2-trichloro-1-(3-n-butyl selenourea)-ethyl] cinnamamide;
(10) (2E)-N-[2,2,2-trichloro-1-(3-benzyl selenourea)-ethyl] cinnamamide;
(11) (2E)-N-[2,2,2-trichloro-1-(3-n-propyl selenourea)-ethyl] cinnamamide;
(12)(2E)-N-{2,2,2-trichloro-1-[3-(3-chloro-2-methylphenyl)selenourea-ethyl}cinnamamide;
(13) (2E)-N-{2,2,2-trichloro-1-[3-(2,4-dichlorophenyl) selenourea]-ethyl}cinnamamide;
(14) (2E)-N-{2,2,2-trichloro-1-[3-(4-methoxyphenyl) selenourea]-ethyl} cinnamamide;
(15) (2E)-N-{2,2,2-trichloro-1-[3-(2-bromophenyl) selenourea]-ethyl} cinnamamide;
(16) (2E)-N-{2,2,2-trichloro-1-[3-(2,3-dimethylphenyl) selenourea]-ethyl}cinnamamide;
(17) (2E)-N-[2,2,2-trichloro-1-(3-phenyl selenourea)-ethyl] cinnamamide;
(18) (2E)-N-{2,2,2-trichloro-1-[3-(2-chlorophenyl) selenourea]-ethyl} cinnamamide;
(19) (2E)-N-{2,2,2-trichloro-1-[3-(3-bromophenyl) selenourea]-ethyl} cinnamamide;
(20) (2E)-N-{2,2,2-trichloro-1-[3-(2-chlorobenzyl) selenourea]-ethyl} cinnamamide;
(21) (2E)-N-[2,2,2-trichloro-1-(3-isobutyl selenourea)-ethyl]cinnamamide;
(22) (2E)-N-{2,2,2-trichloro-1-[3-(4-hydroxyphenyl) selenourea]-ethyl} cinnamamide;
(23) (2E)-N-{2,2,2-trichloro-1-[3-(4-bromophenyl) selenourea]-ethyl} cinnamamide;
(24) (2E)-N-[3-methyl-1-(3-phenyl thioureido) butyl]-3-(3,4,5-trimethoxyphenyl) acrylamide;
(25) (2E)-N-[3-methyl-1-(3-pyridin-3-yl thioureido) butyl]-3-(3,4,5-trimethoxyphenyl) acrylamide;
(26) (2E)-N-[2,2-dimethyl-1-(3-phenyl thioureido) propyl]-3-(3,4,5-trimethoxyphenyl) acrylamide;
(27) (2E)-N-[2,2-dimethyl-1-(3-pyridin-3-yl thioureido) propyl]-3-(3,4,5-trimethoxyphenyl)acrylamide;
(28) (2E)-N-[cyclopropyl-(3-phenyl thioureido)-methyl]-3-(3,4,5-tri methoxyphenyl)acrylamide;

(29) (2E)-N-[cyclopropyl-(3-pyridin-3-yl thioureido)-methyl]-3-(3,4,5-trimethoxyphenyl) acrylamide;
(30) (2E)-N-[cyclopropyl-(3-pyridin-2-yl thioureido)-methyl]-3-(3,4,5-trimethoxyphenyl) acrylamide;
(31) (2E)-N-[3-methyl-1-(3-pyridin-2-yl thioureido) butyl]-3-(3,4,5-trimethoxyphenyl) acrylamide;
(32) (2E)-N-[3,3-dimethyl-1-(3-phenyl thioureido) butyl]-3-(3,4,5-trimethoxyphenyl) acrylamide;
(33) (2E)-N-[3,3-dimethyl-1-(3-pyridin-3-yl thioureido) butyl]-3-(3,4,5-trimethoxyphenyl) acrylamide;
(34) (2E)-N-[3,3-dimethyl-1-(3-pyridin-2-yl thioureido) butyl]-3-(3,4,5-trimethoxyphenyl) acrylamide;
(35) (2E)-N-[2-methyl-1-(3-pyridin-2-yl thioureido) propyl]-3-(3,4,5-trimethoxyphenyl) acrylamide;
(36) (2E)-N-[2-methyl-1-(3-phenyl thioureido) propyl]-3-(3,4,5-trimethoxyphenyl) acrylamide;
(37) (2E)-N-[cyclopropyl-(3-pyridin-2-yl thioureido)-methyl] cinnamamide;
(38) (2E)-N-[3-methyl-1-(3-phenyl thioureido) butyl] cinnamamide;
(39) (2E)-N-[3,3-dimethyl-1-(3-phenyl thioureido) butyl] cinnamamide;
(40) (2E)-N-[2,2-dimethyl-1-(3-phenyl thioureido) propyl] cinnamamide;
(41) (2E)-N-[cyclopropyl-(3-phenyl thioureido)-methyl] cinnamamide;
(42) (2E)-N-[2-methyl-1-(3-phenyl thioureido) propyl] cinnamamide;
(43) (2E)-N-[3-methyl-1-(3-methyl thioureido) butyl]-3-(3,4,5-trimethoxyphenyl) acrylamide;
(44) (2E)-N-[2,2-dimethyl-1-(3-o-methyl phenyl thioureido) propyl]-3-(3,4,5-trimethoxyphenyl) acrylamide;
(45) (2E)-N-[cyclopropyl-(3-o-methyl phenyl thioureido)-methyl]-3-(3,4,5-trimethoxyphenyl) acrylamide;
(46) N-[3,3-dimethyl-1-(3-o-methyl phenyl thioureido) butyl] cinnamamide;
(47) N-[3-methyl-1-(3-o-methyl phenyl thioureido) butyl] cinnamamide;
(48) N-[2,2-dimethyl-1-(3-o-methyl phenyl thioureido) propyl] cinnamamide;
(49) N-[cyclopropyl-(3-o-methyl phenyl thioureido)-methyl] cinnamamide;
(50) (2E)-N-{1-[3-(4-methoxyphenyl) thioureido]-2-methylpropyl}-3-(3,4,5-trimethoxyphenyl) acrylamide;
(51) (2E)-N-[1-(3-cyclohexyl thioureido)-3-methylbutyl]-3-(3,4,5-trimethoxyphenyl) acrylamide;
(52) (2E)-N-[1-(3-cyclohexyl thioureido)-2,2-dimethylpropyl]-3-(3,4,5-trimethoxyphenyl) acrylamide;
(53) (2E)-N-[1-(3-cyclohexyl thioureido)-2-methylpropyl]-3-(3,4,5-trimethoxyphenyl) acrylamide;
(54) N-[1-(3-cyclohexyl thioureido)-3-methylbutyl] cinnamamide;
(55) N-[1-(3-cyclohexyl thioureido)-2-methylpropyl] cinnamamide; and
(56) N-[1-(3-cyclohexyl thioureido)-2,2-dimethylpropyl] cinnamamide.

In a second aspect, the invention relates to a method for preparing the compound of Formula I, an isomer, a pharmaceutically acceptable salt, or a solvate thereof according to the first aspect of the invention, wherein when $R_4$ is haloalkyl, the method comprises the following reaction scheme:

firstly, a corresponding aldehyde is reacted with malonic acid in a pyridine solution at 80° C. to prepare a compound C;

the compound C is reacted with acyl chloride such as p-toluenesulfonyl chloride in DCM at room temperature or under heating to produce an active ester E, and the active ester E is then reacted with ammonia water under reflux to prepare a compound F; or the compound C in anhydrous dichloromethane is reacted with oxalyl chloride in the presence of DMF as a catalyst in an ice-water bath, and after the reaction, concentrated ammonia water at 0° C. is then added to produce a compound F;

the compound F is reacted with an aldehyde hydrate substituted with trihalomethyl, such as trihalo-acetaldehyde, in solvent toluene under reflux to prepare an intermediate G, $SOCl_2$ is added dropwise at room temperature to a solution of the intermediate G in anhydrous THF, and the reaction is carried out in the presence of DMF as a catalyst under heating to a temperature of 60° C. to prepare a chloride H;

the chloride H is then reacted with KACN in anhydrous acetone at 40° C. to produce a corresponding isocyanate I, wherein A has the same meanings as defined in claim 1;

the isocyanate I is reacted with a corresponding substituted amine at 60° C. in anhydrous acetone or anhydrous THF to prepare a compound J of the invention; wherein the product can be separated and purified by standard techniques in the art, for example, extraction, chromatography, crystallization and distillation,

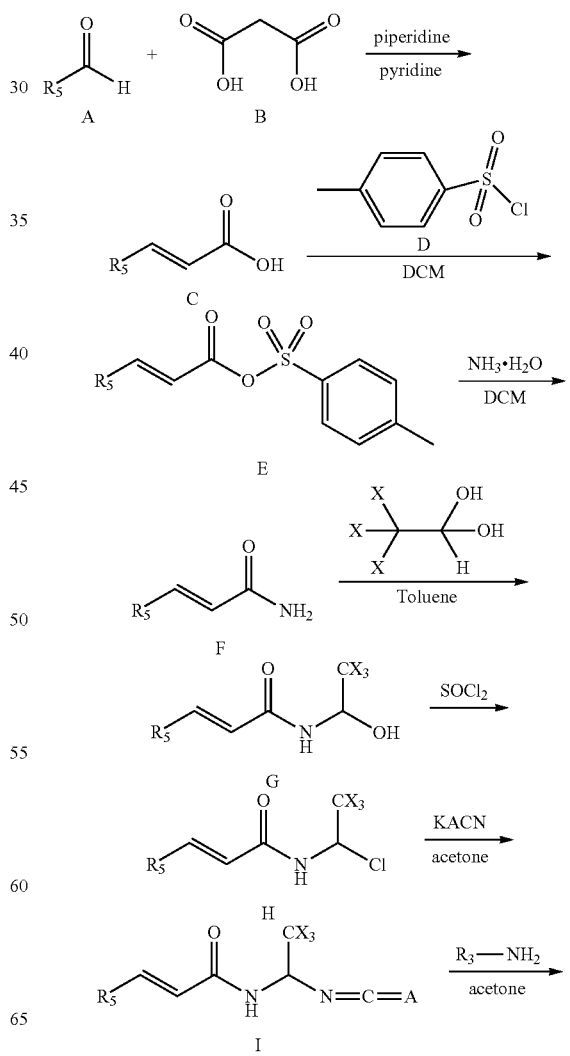

-continued

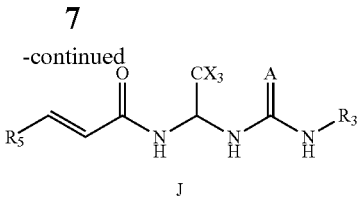

J wherein,

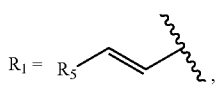

has the same meanings as defined in claim 1.

The method for preparing the compound of Formula I, an isomer, a pharmaceutically acceptable salt, or a solvate thereof according to the second aspect of the invention, wherein when $R_4$ is hydrogen or aliphatic group, the method comprises the following scheme:

firstly, a corresponding aldehyde is reacted with malonic acid at 80° C. in a pyridine solution to prepare a compound C;

the compound C is reacted with acyl chloride such as p-toluenesulfonyl chloride in DCM at room temperature or under heating to produce an active ester E, and the active ester E is then reacted with ammonia water under reflux to prepare a compound F; or the compound C in anhydrous dichloromethane is reacted with oxalyl chloride in the presence of DMF as catalyst in an ice-water bath, and after the reaction, concentrated ammonia water at 0° C. is added to produce a compound F;

the compound F in toluene, together with benzotriazole and a corresponding aliphatic aldehyde, was subjected to Mannich reaction under reflux to prepare an intermediate L; and the intermediate L and an intermediate K in anhydrous THF as a solvent in the presence of NaH as a catalyst at room temperature are subjected to substitution reaction to prepare a compound W of the invention, wherein the intermediate K is prepared by the following steps: a corresponding amine is reacted with $CS_2$, $ICH_3$ in DMSO or DMF, with the addition of a strong base KOH, NaOH or NaH under heating to produce an intermediate N, and then the intermediate N is subjected to aminolysis by the addition of ammonia water under methanol or ethanol reflux conditions; wherein the product can be separated and purified by standard techniques in the art, for example, extraction, chromatography, crystallization and distillation,

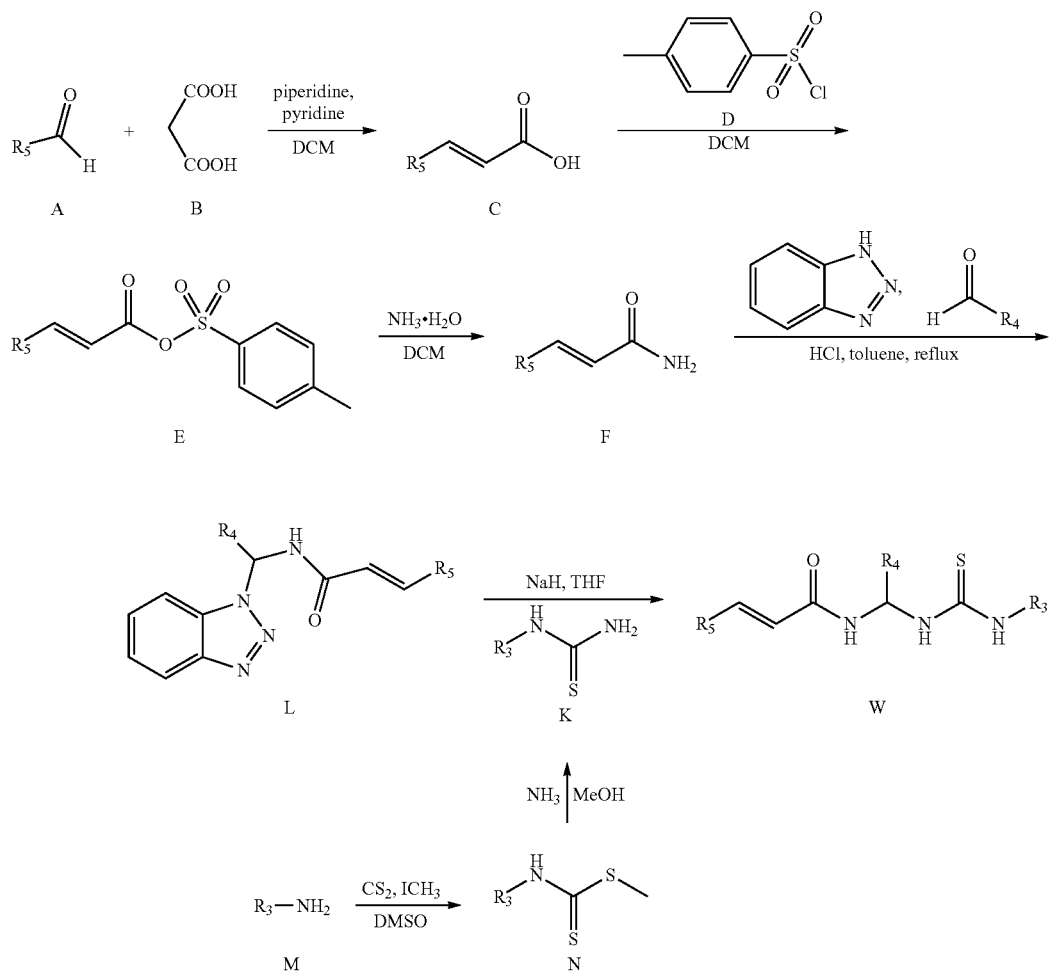

wherein, when $R_1$ is not cycloalkyl,

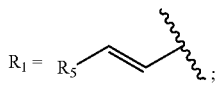

when $R_1$ is cycloalkyl, the starting material is the compound F, i.e. cycloalkyl formamide, in the above scheme; $R_1$ has the same meanings as defined in claim 1.

In a third aspect, the invention relates to a pharmaceutical composition, comprising the compound of Formula I, an isomer, a pharmaceutically acceptable salt, or a solvate thereof according to the first aspect of the invention, and a pharmaceutically acceptable carrier, excipient or diluent.

In a fourth aspect, the invention relates to use of the compound of Formula I, an isomer, a pharmaceutically acceptable salt, or a solvate thereof according to the first aspect of the invention in manufacture of a medicament for prevention and/or treatment of a drug-resistant tumor or a disease or disorder caused by a drug-resistant bacterium.

In a fifth aspect, the invention relates to use of the compound of Formula I, an isomer, a pharmaceutically acceptable salt, or a solvate thereof according to the first aspect of the invention in manufacture of a medicament for prevention and/or treatment of a tumor, a neurodegenerative disease, an allogeneic graft rejection, or an infection-associated disease or disorder; preferably, the tumor, neurodegenerative disease, allogeneic graft rejection, or infection-associated disease or disorder is a disease or disorder caused by Heat shock protein 70 (Hsp70).

The use according to the fourth aspect or the fifth aspect of the invention, the tumor is selected from breast cancer, prostatic cancer, liver cancer, esophageal cancer, stomach cancer, and skin cancer.

The use according to the fifth aspect of the invention, wherein the neurodegenerative disease is selected from Alzheimer's disease, amyotrophic lateral sclerosis, ataxia-telangiectasis, Creutzfeldt-Jakob disease, Huntington's disease, Spinocerebellar Atrophy, multiple sclerosis, Parkinson's Disease, primary lateral sclerosis, and spinal muscular atrophy.

In a sixth aspect, the invention relates to a method for preventing and/or treating a drug-resistant tumor or a disease or disorder caused by a drug-resistant bacterium, comprising administering to a subject in need thereof a therapeutically and/or prophylactically effective amount of the compound of Formula I, an isomer, a pharmaceutically acceptable salt, or a solvate thereof according to the first aspect of the invention.

In a seventh aspect, the invention relates to a method for preventing and/or treating a tumor, a neurodegenerative disease, an allogeneic graft rejection, or an infection-associated disease or disorder, comprising administering to a subject in need thereof a therapeutically and/or prophylactically effective amount of the compound of Formula I, an isomer, a pharmaceutically acceptable salt, or a solvate thereof according to the first aspect of the invention; preferably, the tumor, neurodegenerative disease, allogeneic graft rejection, or infection-associated disease or disorder is a disease or disorder caused by Heat shock protein 70 (Hsp70).

The method according to the sixth aspect or the seventh aspect of the invention, wherein the tumor is selected from breast cancer, prostatic cancer, liver cancer, esophageal cancer, stomach cancer, and skin cancer.

The method according to the seventh aspect of the invention, wherein the neurodegenerative disease is selected from Alzheimer's disease, amyotrophic lateral sclerosis, ataxia-telangiectasis, Creutzfeldt-Jakob disease, Huntington's disease, Spinocerebellar Atrophy, multiple sclerosis, Parkinson's Disease, primary lateral sclerosis, and spinal muscular atrophy.

In an eighth aspect, the invention relates to the compound of Formula I, an isomer, a pharmaceutically acceptable salt, or a solvate thereof according to the first aspect of the invention for use in prevention and/or treatment of a drug-resistant tumor or a disease caused by a drug-resistant bacterium.

In a ninth aspect, the invention relates to the compound of Formula I, an isomer, a pharmaceutically acceptable salt, or a solvate thereof according to the first aspect of the invention for use in prevention and/or treatment of a tumor, a neurodegenerative disease, an allogeneic graft rejection, or an infection-associated disease or disorder, preferably, the tumor, neurodegenerative disease, allogeneic graft rejection, or infection-associated disease or disorder is a disease or disorder caused by Heat shock protein 70 (Hsp70).

The compound of Formula I, an isomer, a pharmaceutically acceptable salt, or a solvate thereof according to the eighth aspect or the ninth aspect of the invention, wherein the tumor is selected from breast cancer, prostatic cancer, liver cancer, esophageal cancer, stomach cancer, and skin cancer.

The compound of Formula I, an isomer, a pharmaceutically acceptable salt, or a solvate thereof according to the ninth aspect of the invention, wherein the neurodegenerative disease is selected from Alzheimer's disease, amyotrophic lateral sclerosis, ataxiatelangiectasis, Creutzfeldt-Jakob disease, Huntington's disease, Spinocerebellar Atrophy, multiple sclerosis, Parkinson's Disease, primary lateral sclerosis, and spinal muscular atrophy.

In a tenth aspect, the invention relates to a method for combating/reversing drug resistance of a bacterium in a cell or drug resistance of a tumor cell, comprising administering to the cell an effective amount of the compound of Formula I, an isomer, a pharmaceutically acceptable salt, or a solvate thereof according to the first aspect of the invention.

In an eleventh aspect, the invention relates to a method for inhibiting the expression of Heat shock protein 70 (Hsp70) in a cell, comprising administering to the cell an effective amount of the compound of Formula I, an isomer, a pharmaceutically acceptable salt, or a solvate thereof according to the first aspect of the invention.

The method according to the tenth aspect or the eleventh aspect of the invention, wherein the cell is a cell line or a cell from a subject.

The method according to the tenth aspect or the eleventh aspect of the invention, wherein the tumor cell is selected from a breast cancer cell, prostatic cancer cell, liver cancer cell, esophageal cancer cell, stomach cancer cell, and skin cancer cell.

The method according to the tenth aspect or the eleventh aspect of the invention, wherein the method is carried out in vitro.

The method according to the tenth aspect or the eleventh aspect of the invention, wherein the method is carried out in vivo.

A twelfth aspect, the invention relates to use of the compound of Formula I, an isomer, a pharmaceutically acceptable salt, or a solvate thereof according to the first aspect of the invention in manufacture of an agent, wherein the agent is used for combating/reversing drug resistance of a bacterium in a cell or drug resistance of a tumor cell.

In a thirteenth aspect, the invention relates to use of the compound of Formula I, an isomer, a pharmaceutically acceptable salt, or a solvate thereof according to the first aspect of the invention in manufacture of an agent, wherein the agent is used for inhibiting activity of Heat shock protein 70 (Hsp70) in a cell.

The use according to the twelfth aspect or the thirteenth aspect, wherein the cell is a cell line, or a cell from a subject.

The use according to the twelfth aspect or the thirteenth aspect, wherein the tumor cell is selected from a breast cancer cell, prostatic cancer cell, liver cancer cell, esophageal cancer cell, stomach cancer cell, and skin cancer cell.

The use according to the twelfth aspect or the thirteenth aspect, wherein the agent is used in an in vitro method.

The use according to the twelfth aspect or the thirteenth aspect, wherein the agent is used in an in vivo method.

In a fourteenth aspect, the invention relates to the compound of Formula I, an isomer, a pharmaceutically acceptable salt, or a solvate thereof according to the first aspect of the invention for use in combating/reversing drug resistance of a bacterium in a cell or drug resistance of a tumor cell.

In a fifteenth aspect, the invention relates to the compound of Formula I, an isomer, a pharmaceutically acceptable salt, or a solvate thereof according to the first aspect of the invention for use in inhibiting activity of Heat shock protein 70 (Hsp70) in a cell.

The compound of Formula I, an isomer, a pharmaceutically acceptable salt, or a solvate thereof according to the fourteenth aspect or the fifteenth aspect of the invention, wherein the cell is a cell line, or a cell from a subject.

The compound of Formula I, an isomer, a pharmaceutically acceptable salt, or a solvate thereof according to the fourteenth aspect or the fifteenth aspect of the invention, wherein the tumor cell is selected from a breast cancer cell, prostatic cancer cell, liver cancer cell, esophageal cancer cell, stomach cancer cell, and skin cancer cell.

The compound of Formula I, an isomer, a pharmaceutically acceptable salt, or a solvate thereof according to the fourteenth aspect or the fifteenth aspect of the invention for use in an in vitro method.

The compound of Formula I, an isomer, a pharmaceutically acceptable salt, or a solvate thereof according to the fourteenth aspect or the fifteenth aspect of the invention for use in an in vivo method.

In a sixteenth aspect, the invention relates to a kit for combating/reversing drug resistance of a bacterium in a cell or drug resistance of a tumor cell, comprising the compound of Formula I, an isomer, a pharmaceutically acceptable salt, or a solvate thereof according to the first aspect of the invention, and optionally an instruction.

In a seventeenth aspect, the invention relates to a kit for inhibiting activity of Heat Shock protein 70 (Hsp 70) in a cell, comprising the compound of Formula I, an isomer, a pharmaceutically acceptable salt, or a solvate thereof according to the first aspect of the invention, and optionally an instruction.

BENEFICIAL EFFECTS OF THE INVENTION

The invention provides a compound of a novel structure, and it is demonstrated experimentally that the compound of the invention and Lapatinib have a synergistic effect, can inhibit tumor growth effectively, and effectively reverse resistance to Lapatinib in vitro. The invention provides a class of Hsp70 inhibitors having a high activity and a novel structure, solve the problem concerning drug resistance of tumors, enhance the effect of treating tumors, and provide a new medical strategy for treatment of tumors in clinic.

The terms used to describe the invention in the description and claims of the application are defined as follows. For specific terms, if the meanings defined in the application are different from the meanings generally understood by a person skilled in the art, the meanings defined in the application shall prevail; if the application does not provide any definition, the terms have the meanings generally understood by a person skilled in the art.

The names of the compounds of the invention correspond to the formulae, and if the compound names are not consistent with the formulae, the formulae shall prevail, or it can be deduced by a person skilled in the art based on the context of the invention and the knowledge of the person skilled in the art.

The term "alkyl" used herein refers to a saturated, linear or branched monovalent hydrocarbonyl. "C1-10alkyl" refers to linear or branched alkyl having 1-10 carbon atoms, such as methyl, ethyl, propyl, isopropyl, n-butyl, isobutyl, sec-butyl, tert-butyl, pentyl, 2-pentyl, isopentyl, neopentyl, hexyl, 2-hexyl, 3-hexyl, 3-methylpentyl, heptyl, octyl. The term "C1-6alkyl" refers to linear or branched alkyl having 1-6 (i.e., 1, 2, 3, 4, 5 or 6) carbon atoms, which is typically methyl, ethyl, n-propyl, isopropyl, n-butyl, isobutyl, sec-butyl, tert-butyl, neopentyl, pentyl, hexyl, etc. Similarly, the term "C1-3alkyl" refers to linear or branched alkyl having 1, 2 or 3 carbon atoms, i.e., methyl, ethyl, n-propyl and isopropyl. The alkyl of the invention is preferably C1-10alkyl, more preferably C1-6alkyl, more preferably C1-3alkyl.

The term "substituted alkyl" used herein refers to a group obtained by substituting the alkyl defined above by one, two or three substituents selected from a group consisting of C1-6alkyl, C1-6alkoxyl, cyano, halogen, hydroxyl, amino, nitro, mono-C1-6alkyl amino, di-C1-6alkyl amino, C2-6alkenyl, C2-6 alkynyl, C1-6haloalkyl and C1-6haloalkoxyl. Examples of substituted alkyl in the invention include trichloromethane.

The term "C2-6alkenyl" used herein refers to an alkenyl having 2-6 carbon atoms, and having 1, 2 or 3 carbon-carbon double bonds, when there are more than one carbon-carbon double bond, the carbon-carbon double bonds are conjugated or not. Examples of C2-6alkenyl in the invention include vinyl or propenyl.

The term "C2-6 alkynyl" used herein refers to an alkynyl having 2-6 carbon atoms, and having 1, 2 or 3 carbon-carbon triple bonds, when there are more than one carbon-carbon triple bond, the carbon-carbon triple bonds are conjugated or not. Examples of C2-6 alkynyl in the invention include acetenyl or propinyl.

The term "C1-6alkoxyl" used herein refers to an alkoxyl having 1-6 carbon atoms. Examples of C1-6alkoxyl in the invention include methoxyl.

The term "halogen" used herein refers to F, Cl, Br and I.

The term "aryl" used herein refers to a monocyclic or dicyclic aromatic system comprising at least one unsaturated aromatic ring, preferably the aryl having 6~10 (i.e., 6, 7, 8, 9 or 10) carbon atoms. Examples of aryl in the invention include phenyl, naphthyl, 1,2,3,4-tetrahydro naphthyl, indenyl, etc.

The term "substituted aryl" used herein refers to a group obtained by substituting the aryl defined above by one, two or three substituents selected from a group consisting of C1-6alkyl, C1-6alkoxyl, cyano, halogen, hydroxyl, amino, nitro, mono-C1-6alkyl amino, di-C1-6alkyl amino, C2-6alkenyl, C2-6 alkynyl, C1-6haloalkyl, and C1-6haloalkoxyl. Examples of substituted aryl in the invention include 2-chlorophenyl, 4-chlorophenyl, 2-methoxyphenyl, 4-methoxyphenyl, 3-nitrophenyl, 2,4-difluorophenyl, 4-fluorophenyl, 2-methyl-3-chlorophenyl, 2,4-dichlorophenyl, 2-bromophenyl, 3-bromophenyl, 4-bromophenyl, 2-methylphenyl, 2,3-dimethylphenyl, 4-hydroxyphenyl, etc.

The term "aromatic heterocyclyl" used herein refers to an unsaturated, monocyclic or dicyclic aromatic system optionally substituted by at least one heteroatom independently selected from N, O, and S, preferably the aromatic heterocyclyl having 5~10 (i.e., 5, 6, 7, 8, 9 or 10) atoms. Examples of "aromatic heterocyclyl" in the invention include, but are not limited to thienyl, 2-pyridyl, 3-pyridyl, thiazolyl, isothiazolyl, furyl, pyrrolyl, triazolyl, imidazolyl, triazinyl, oxadiazolyl, oxazolyl, isoxazolyl, pyrazolyl, imidazolonyl, oxazole, thiazolonyl, tetrazolyl, thiadiazolyl, benzimidazolyl, benzoxazolyl, benzothiazolyl, tetrahydrotriazolopyridinyl, tetrahydrotriazolopyrimidinyl, benzofuranyl, benzothiophenyl, thianaphthenyl, indolyl, isoindolyl, pyridinonyl, pyridazinyl, pyrazinyl, pyrimidinyl, quinolyl, phthalazinyl, quinoxalinyl, quinazolinyl, imidazopyridinyl, oxazolopyridinyl, thiazolopyridinyl, imidazopyridazinyl, oxazolopyridazinyl, thiazolopyridazinyl, pteridyl, furazanyl, benzotriazolyl, pyrazolopyridinyl, purinyl, etc.

The term "substituted aromatic heterocyclyl" used herein refers to a group obtained by substituting the aromatic heterocyclyl defined above by one, two or three substituents selected from a group consisting of C1-6alkyl, C1-6alkoxyl, cyano, halogen, hydroxyl, amino, nitro, mono-C1-6alkyl amino, di-C1-6alkyl amino, C2-6alkenyl, C2-6 alkynyl, C1-6haloalkyl, and C1-6haloalkoxyl.

The term "cycloalkyl" used herein refers to a saturated carbocyclic ring group having 3, 4, 5, 6, 7, 8, 9 or 10 carbon atoms. The cycloalkyl may be a monocyclic or polycyclic fused system, and may be fused to an aromatic ring. Examples of the group in the invention include cyclopropyl, cyclobutyl, cyclopentyl and cyclohexyl, etc.

The term "substituted cycloalkyl" used herein refers to a group obtained by substituting the cycloalkyl defined above by one, two or three substituents selected from a group consisting of C1-6alkyl, C1-6alkoxyl, cyano, halogen, hydroxyl, amino, nitro, mono-C1-6alkyl amino, di-C1-6alkyl amino, C2-6alkenyl, C2-6 alkynyl, C1-6haloalkyl, and C1-6haloalkoxyl.

The term "heterocyclyl" used herein refers to a saturated, partially saturated, or unsaturated monocyclic or dicyclic system substituted by at least one and at most four heteroatoms independently selected from N, O or S, preferably the heterocyclyl having 4-10 (i.e., 4, 5, 6, 7, 8, 9 or 10) atoms, provided that the heterocyclyl ring does not comprise two neighboring O or S atoms. A preferred heterocyclyl includes, but is not limited to pyrrolidinyl, tetrahydrofuryl, dihydrofuryl, tetrahydrothienyl, piperidinyl, morpholinyl, or piperazinyl, etc.

The term "substituted heterocyclyl" used herein refers to a group obtained by substituting the heterocyclyl defined above by one, two or three substituents selected from a group consisting of C1-6alkyl, C1-6alkoxyl, cyano, halogen, hydroxyl, amino, nitro, mono-C1-6alkyl amino, di-C1-6alkyl amino, C2-6alkenyl, C2-6 alkynyl, C1-6haloalkyl, and C1-6haloalkoxyl.

The term "arylalkyl" used herein refers to the alkyl defined above substituted by one or more aryl defined above. A preferred arylalkyl is aryl-C1-3alkyl. Examples of arylalkyl in the invention include benzyl and phenyl ethyl, etc.

The term "substituted arylalkyl" used herein refers to the alkyl defined above substituted by one or more substituted aryl defined above. Examples of substituted arylalkyl in the invention include 2-chlorobenzyl.

The term "arylalkenyl" used herein refers to an alkenyl substituted by one, two or three aryl defined above, wherein the alkenyl has one, or two or more carbon-carbon double bonds conjugated with the aryl. A preferred arylalkenyl is aryl-C2-6alkenyl. Examples of arylalkenyl in the invention include phenyl vinyl, etc.

The term "substituted arylalkenyl" used herein refers to an alkenyl substituted by one or more substituted aryl defined above, wherein the alkenyl has one or two or more carbon-carbon double bonds conjugated with the substituted aryl. A preferred substituted arylalkenyl is substituted aryl-C2-6alkenyl. Examples of arylalkenyl in the invention include 3,4,5-trimethoxyphenylvinyl, etc.

The term "aromatic heterocyclylalkyl" used herein refers to the alkyl defined above substituted by the aromatic heterocyclyl defined above. A preferred aromatic heterocyclylalkyl is 5- or 6-membered heteroaryl-C1-3-alkyl. Examples of heteroarylalkyl in the invention include pyridylethyl, etc.

The term "substituted aromatic heterocyclylalkyl" used herein refers to the alkyl defined above substituted by the substituted aromatic heterocyclyl defined above.

The term "heterocyclylalkyl" used herein refers to the alkyl defined above substituted by the heterocyclyl defined above. A preferred heterocyclylalkyl is a 5 or 6 membered heterocyclyl-C1-3-alkyl. Examples of heterocyclylalkyl in the invention include tetrahydropyranylmethyl.

The term "substituted heterocycloalkyl" used herein refers to the alkyl defined above substituted by the substituted heterocyclyl defined above.

The term "pharmaceutically acceptable salt" used herein refers to a salt of the compound of the invention which is pharmaceutically acceptable and has the desired pharmacological activity of the parent compound. Such a salt includes an acid addition salt formed with inorganic acid or organic acid, the inorganic acid includes hydrochloric acid, hydrobromic acid, sulphuric acid, nitric acid, phosphoric acid, etc.; the organic acid includes acetic acid, propionic acid, hexanoic acid, cyclopentylpropionic acid, glycolic acid, pyruvic acid, lactic acid, malonic acid, succinic acid, malic acid, maleic acid, fumaric acid, tartaric acid, citric acid, benzoic acid, cinnamic acid, mandelic acid, methanesulfonic acid, ethanesulfonic acid, benzenesulfonic acid, naphthalene sulfonic acid, camphor sulfonic acid, glucoheptonic acid, gluconic acid, glutamic acid, naphtholcarboxylic acid, salicylic acid, stearic acid, muconic acid, etc.; or a salt formed by the substitution of an acidic proton of the parent compound with a metal ion such as alkali metal ion or alkali earth metal ion; or a coordination compound formed with organic base such as ethanolamine, diethanolamine, triethanolamine, N-methylglucosamine, etc.

The term "solvate" used herein refers to a substance formed by the binding of the compound of the invention with a pharmaceutically acceptable solvent. The pharmaceutically acceptable solvent includes water, ethanol, acetic acid, etc. The solvate includes stoichiometric solvate and non-stoichiometric solvate, preferably hydrate. The compound of the invention may be crystallized or re-crystallized in water or various organic solvents, in this case, various solvates are formed.

The term "subject" used herein refers to mammal and human, preferably human.

A person skilled in the art can understand that the compound of the invention has stereomers, such as cis-trans-isomer and optical isomers, e.g., enantiomers and diastereomers, etc. Therefore, when the compound of the invention is mentioned in the description, the compound of the invention includes the compound of formula I, a pharmaceutically acceptable salt, a stereomer and a solvate thereof. The compound of the invention further includes its active metabolite in mammal.

In the invention, the drug resistance refers to resistance to a chemically therapeutic drug in a microorganism, parasite or tumor cell, i.e., the sensitivity is reduced, and once drug resistance occurs, the chemically therapeutic effect of the drug is reduced significantly.

In the embodiments of the invention, the drug resistance refers to resistance to Lapatinib.

In the invention, the combating/reversing drug resistance of a bacterium in a cell or drug resistance of tumor cell refers to regain or enhance sensitivity to drug in a bacterium or a tumor cell.

The section "Specific modes for carrying out the Invention" in the description illustrates the methods for preparing the compounds of the invention and their anti-tumor effects.

The pharmaceutical composition of the invention comprises the compound of formula I, an isomer, a pharmaceutically acceptable salt, or a solvent such as a hydrate thereof of the invention, and one or more suitable, pharmaceutically acceptable carriers. The pharmaceutically acceptable carriers herein include, but are not limited to: ion exchanger, aluminum oxide, aluminum stearate, lecithin, serum protein such as human serum albumin, buffer substance such as phosphate, glycerol, sorbic acid, potassium sorbate, a partial glyceride mixture of saturated plant fatty acid, water, salt or electrolyte, such as protamine sulfate, disodium hydrogen phosphate, potassium hydrogen phosphate, sodium chloride, zinc salt, colloided silica, magnesium trisilicate, polyvinylpyrrolidone, cellulose substance, polyethylene glycol, carboxymethylcellulose sodium, polyacrylic ester, beewax, and lanolin.

The pharmaceutical composition comprising the compound of the invention can be administered by any of the following ways: oral administration, inhalation with aerohaler, rectal administration, intranasal administration, buccal administration, topical administration, parenteral administration such as subcutaneous, intravenous, intramuscular, intraperitoneal, intrathecal, intraventricular, intrasternal and intracranial injection or input, or administration by virtue of an explanted reservoir, preferably oral, intraperitoneal or intravenous administration.

When orally administered, the compound of the invention may be prepared in any orally acceptable form, including, but not limited to tablet, capsule, aqueous solution, or aqueous suspension. The carriers for use in a tablet generally include lactose and maize starch, in addition, lubricants such as magnesium stearate can also be added. Diluents for use in capsules generally include lactose and dry maize starch. Aqueous suspension is generally obtained by mixing an active ingredient with a suitable emulsifying agent and a suitable suspending agent. If necessary, a sweetening agent, a flavoring agent or a coloring agent may be added to the above oral preparation.

When topical administrated, particularly when treating neurogenic disease at the affected part or organ that is easily accessible by topical application, such as eyes, skin or lower intestine, the compound of the invention may be prepared in different forms for topical application depending on the affected part or organ, in particular, when topical administrated to eyes, the compound of the invention may be prepared in a form of micronized suspension or solution, and the carrier used is a sterile saline that is isotonic and is at a certain pH, wherein preservatives such as chloride benzyl alkoxide may be added or not. For ophthalmic use, the compound may be prepared in a form of ointment such as vasaline ointment.

When topically administered to skin, the compounds of the invention may be prepared in a suitable form of ointments, lotions or creams, wherein the active ingredient is suspended or dissolved in one or more carriers. The carriers for use in ointment preparations include, but are not limited to mineral oil, liquid paraffin, albolene, propylene glycol, polyethylene oxide, polypropylene oxide, emulsion wax and water; carriers for use in lotions and creams include, but are not limited to mineral oil, sorbitan monostearate, Tween 60, hexadecyl ester wax, hexadecene aromatic alcohol, 2-octyl dodecanol, benzyl alcohol, and water.

The compound of the invention may be administered in a form of sterile formulation for injection, including sterile injection water, oil suspension or steril injection solution. The carriers and solvents for use in them include water, Ringer's solution, and liquor natrii chloridi isotonicus. In addition, sterile fixed oil can also be used as solvent or suspension medium, such as monoglyceride or diglyceride.

The dosage of the compound of the invention administered to a subject depends on factors such as the types and severity of diseases or disorders, the characteristics of a subject, such as general health condition, age, gender, body weight and tolerance to a drug, the type of a preparation, the administration route of a drug, and the administration period or interval. A person skilled in the art can determine a suitable dosage depending on these factors and other factors. In general, the compound of the invention may be used in a daily dose of about 1~800 mg for the treatment of tumor, wherein the daily dose may be administered once or for several times as required, and the compound of the invention may be comprised in an amount of 0.1~200 mg, such as 1~100 mg per dosage unit.

SPECIFIC MODES FOR CARRYING OUT THE INVENTION

The embodiments of the invention are described by combining the following examples. However, a person skilled in the art understands that the following examples are only intended to describe the invention, and shall not be regarded as defining the scope of the invention. When the particular conditions are not indicated in Examples, the invention is carried out according to the conventional conditions or the conditions suggested by the manufacturer. The reagents or apparatuses, the manufacturers of which are not indicated, are the conventional products that are commercially available.

The melting point of a compound is measured by RY-1 melting point apparatus, the thermometer is not calibrated. Mass spectrum is measured by Micromass ZabSpec High Resolution Mass Spectrometer (with a resolution of 1000). 1H NMR is measured by JNM-ECA-400 Superconducting NMR Apparatus, at an operating frequency of 1H NMR 400 MHz, 13C NMR 100 MHz.

Example 1 (2E)-N-{2,2,2-trichloro-1-[3-(4-chlorophenyl)selenourea] ethyl}-cinnamamide

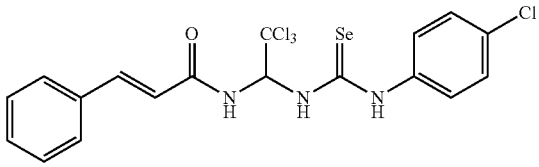

0.7 g (2E)-3-phenyl acrylamide and 1.20 g trichloroacetaldehyde hydrate were added into 30 ml toluene, reacted under reflux for 8 h. Light yellow lamellar crystals were precipitated when cooling to room temperature, and the crystals were collected to obtain 1.20 g (2E)-N-(1-hydroxy-2,2,2-trichloroethyl)-3-phenyl acrylamide. The above obtained product was dissolved in 20 ml anhydrous THF, a drop of DMF was added to catalyze the reaction, and 1.2 ml SOCl$_2$ was added dropwise at room temperature. The reaction solution was then heated to 60° C., and the reaction was carried out for 2 h. After evaporation of the solvent, grayish yellow solid was obtained. The solid was ground in 30 ml cold petroleum ether, and was filtered to prepare off-white powder, which was dried in vacuum overnight. Under the protection of nitrogen gas, the off-white power was dissolved in anhydrous acetone, and 0.30 g KSeCN was quickly added, and stirred for 15 min at room temperature, then 0.50 g p-chloroaniline was added once, and the reaction was carried out at room temperature for 30 min. 4 g crude silica gel was added to the reaction solution, and was eluted by using a mixed solvent of dichloromethane:methanol=200:1 as eluent, to prepare 0.6 g white floccus (2E)-N-[2,2,2-trichloro-1-[3-(4-chlorophenyl) selenourea] ethyl]-cinnamamide, which was recrystallized in THF to prepare the pure product 0.4 g. 1H-NMR (400 MHz, DMSO-d6) δ6.72-6.76 (d, 1H); δ7.42-7.61 (m, 12H); δ8.44-8.46 (d, 1H); δ8.90-8.92 (d, 1H); δ1D0.77 (s, 1H). MS (TOF) 510.1 (M+).

Example 2 (2E)-N-{2,2,2-trichloro-1-[3-(2-methoxyphenyl)selenourea]-ethyl}cinnamamide

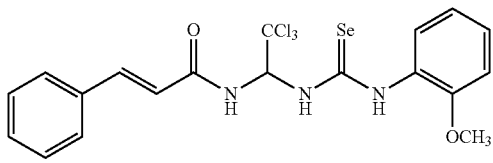

The method of Example 1 was used, except that 2-methoxyaniline was used in place of p-chloroaniline, to prepare 0.20 g white solid. 1H-NMR (400 MHz, DMSO-d6) δ3.82 (s, 3H); δ6.71-6.75 (d, 1H); δ6.94-6.98 (t, 1H); δ7.10-7.12 (d, 1H); δ7.26 (t, 1H); δ7.38-7.62 (m, 8H); δ8.99-9.01 (d, 1H); δ10.29 (s, 1H). MS(TOF) 506.2 (M+).

Example 3 (2E)-N-{2,2,2-trichloro-1-[3-(2-methoxyphenyl)selenourea]-ethyl}-cyclopropylformamide

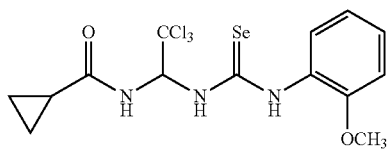

The method of Example 1 was used, except that cyclopropyl formamide was used in place of (2E)-3-phenyl acrylamide, to prepare 60 mg white solid. 1H-NMR (400 MHz, DMSO-d6) δ0.64 (m, 2H); δ0.89 (m, 2H); δ1.16 (m, 1H); δ3.82 (s, 3H); 6.71-6.75 (d, 1H); δ6.94-6.98 (t, 1H); δ7.10-7.12 (d, 1H); δ7.26 (t, 1H); δ7.3 8-7.62 (m, 8H); δ8.99-9.01 (d, 1H); δ10.29 (s, 1H). MS(TOF) 443.6 (M+).

Example 4 (2E)-N-{2,2,2-trichloro-1-[(morpholin-4-selenoformyl) amino]-ethyl}cinnamamide

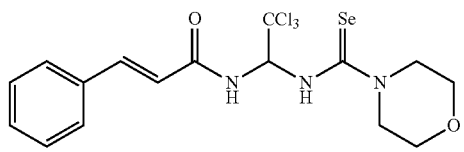

The method of Example 1 was used, except that morpholine was used in place of p-chloroaniline, to prepare 0.23 g white solid. 1H-NMR (400 MHz, DMSO-d6) δ3.60-3.65 (dd, 4H); δ3.90-3.96 (dd, 4H); δ6.78-6.82 (d, 1H); δ7.41-7.46 (m, 3H); δ7.53-7.57 (m, 2H); δ7.65-7.67 (m, 2H); δ7.75-7.80 (t, 1H); δ8.09-8.11 (d, 1H); δ8.36-8.38 (d, 1H). MS(TOF) 472.0 (M+).

Example 5 (2E)-N-{2,2,2-trichloro-1-[3-(3-nitrophenyl)selenourea]-ethyl} cinnamamide

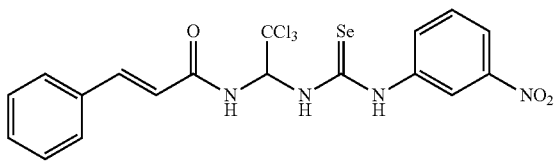

The method of Example 1 was used, except that 3-nitroaniline was used in place of p-chloroaniline, to prepare 0.12 g white solid. 1H-NMR (400 MHz, DMSO-d6) δ6.78-6.82 (d, 1H); δ7.42-7.45 (m, 3H); δ7.55-7.67 (m, 5H); δ7.89-7.91 (dd, 1H); δ8.06-8.07 (dd, 1H); δ8.67 (s, 1H); δ8.83-8.85 (d, 1H); δ9.00-9.02 (d, 1H); δ11.04 (s, 1H). MS(TOF) 521.2 (M+).

Example 6 (2E)-N-{2,2,2-trichloro-1-[3-(2,4-difluorophenyl)selenourea]-ethyl)}cinnamamide

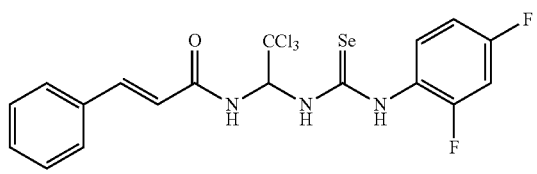

The method of Example 1 was used, except that 2,4-difluoroaniline was used in place of p-chloroaniline, to prepare 0.20 g white solid.

1H-NMR (400 MHz, DMSO-d6) δ6.78-6.85 (d, 1H); δ7.12-7.21 (t, 2H); δ7.40-7.64 (m, 8H); δ8.99-9.12 (m, 2H); δ10.05 (s, 1H). MS(TOF) 512.1 (M+).

Example 7 (2E)-N-{2,2,2-trichloro-1-[(piperidin-1-selenoformyl)amino]-ethyl}cinnamamide

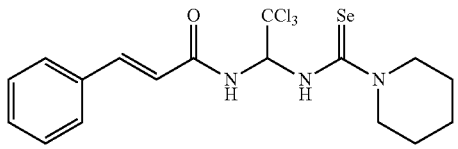

The method of Example 1 was used, except that piperidine was used in place of p-chloroaniline, to prepare 0.19 g white solid. 1H-NMR (400 MHz, DMSO-d6) δ1.55-1.65 (m, 6H); δ3.91 (m, 4H); δ6.73-6.77 (d, 1H); δ7.42-7.46 (m, 3H); δ7.53-7.57 (d, 1H); δ7.60-7.68 (m, 2H); δ7.72-7.77 (s, 1H); δ7.87-7.89 (d, 1H); δ8.39-8.41 (d, 1H). MS(TOF) 468.3 (M+).

Example 8 (2E)-N-{2,2,2-trichloro-1-[3-(4-fluorophenyl)selenourea]-ethyl}cinnamamide

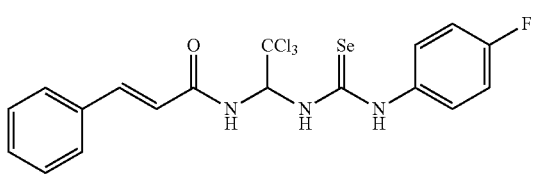

The method of Example 1 was used, except that 4-fluoroaniline was used in place of p-chloroaniline, to prepare 0.30 g white solid. 1H-NMR (400 MHz, DMSO-d6) δ6.71-6.75 (d, 1H); δ7.23-7.27 (t, 2H); δ7.39-7.46 (m, 5H); δ7.53-7.63 (m, 4H); δ8.34 (s, 1H); δ8.94 (d, 1H); δ10.71 (s, 1H). MS(TOF) 494.2 (M+).

Example 9 (2E)-N-[2,2,2-trichloro-1-(3-n-butylselenourea)-ethyl] cinnamamide

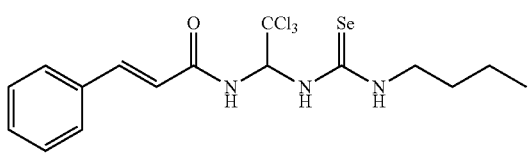

The method of Example 1 was used, except that n-butylamine was used in place of p-chloroaniline, to prepare 0.05 g yellow solid. 1H-NMR (400 MHz, DMSO-d6) δ0.88-0.92 (t, 3H); δ1.29-1.35 (m, 2H); δ1.48-1.53 (m, 2H); δ3.48-3.54 (m, 2H); δ6.76-6.80 (d, 1H); δ7.38-7.60 (m, 7H); δ8.12-8.14 (d, 1H); δ8.67-8.68 (t, 1H); δ8.89-8.91 (d, 1H). MS(TOF) 456.2 (M+).

Example 10 (2E)-N-[2,2,2-trichloro-1-(3-benzylselenourea)-ethyl] cinnamamide

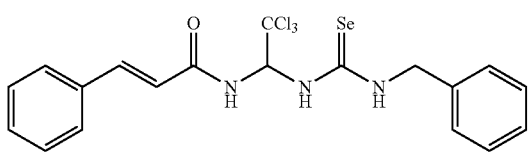

The method of Example 1 was used, except that benzylamine was used in place of p-chloroaniline, to prepare 0.16 g white solid. 1H-NMR (400 MHz, DMSO-d6) δ4.79-4.80 (d, 2H); δ6.78-6.82 (d, 1H); δ7.34-7.44 (m, 8H); δ7.53-7.60 (m, 4H); δ8.31-8.33 (d, 1H); δ9.02-9.04 (d, 1H); δ9.09 (m, 1H). MS(TOF) 490.2 (M+).

Example 11 (2E)-N-[2,2,2-trichloro-1-(3-n-propyl selenourea)-ethyl] cinnamamide

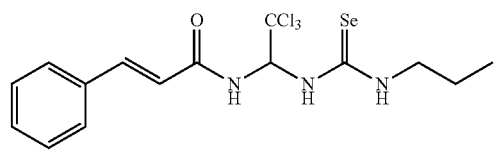

The method of Example 1 was used, except that n-propylamine was used in place of p-chloroaniline, to prepare 0.08 g white solid. 1H-NMR (400 MHz, DMSO-d6) δ0.89-0.91 (t, 3H); δ1.52-1.56 (m, 2H); δ3.44-3.93 (m, 2H); δ6.76-6.80 (d, 1H); δ7.42-7.44 (m, 4H); δ7.51-7.61 (m, 3H); δ8.15-8.18 (d, 1H); δ8.70-8.72 (t, 1H); δ8.93-8.95 (d, 1H). MS(TOF) 442.2 (M+).

Example 12 (2E)-N-{2,2,2-trichloro-1-[3-(3-chloro-2-methylphenyl) selenourea]-ethyl}cinnamamide

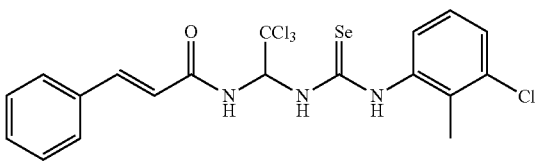

The method of Example 1 was used, except that 2-methyl-3-chloroaniline was used in place of p-chloroaniline, to prepare 0.15 g white solid. 1H-NMR (400 MHz, DMSO-d6) δ2.21 (s, 3H); δ6.70-6.74 (d, 1H); δ7.21-7.31 (m, 2H); δ7.41-7.46 (m, 4H); δ7.54-7.58 (d, 1H); δ7.62-7.64 (m, 3H); δ8.94 (s, 1H); δ10.49 (s, 1H). MS(TOF) 424.7 (M+).

Example 13 (2E)-N-{2,2,2-trichloro-1-[3-(2,4-dichlorophenyl) selenourea]-ethyl}cinnamamide

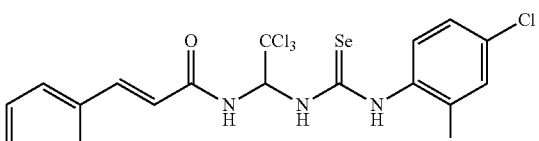

The method of Example 1 was used, except that 2,4-dichloroaniline was used in place of p-chloroaniline, to prepare white 0.15 g solid. 1H-NMR (400 MHz, DMSO-d6) δ6.76-6.80 (d, 1H); δ7.40-7.45 (m, 4H); δ7.54-7.63 (m, 3H); δ7.78-7.91 (m, 3H); δ8.84-8.86 (d, 1H); δ8.96-8.98 (d, 1H); δ11.04 (s, 1H). MS(TOF) 545.1 (M+).

Example 14 (2E)-N-{2,2,2-trichloro-1-[3-(4-methoxyphenyl)selenourea]-ethyl}cinnamamide

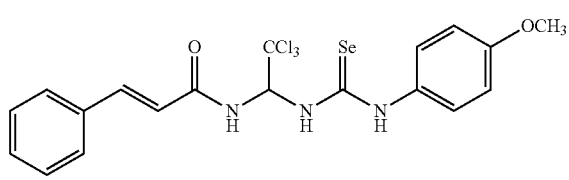

The method of Example 1 was used, except that 4-methoxyaniline was used in place of p-chloroaniline, to prepare 0.15 g white solid. 1H-NMR (400 MHz, DMSO-d6) δ3.76 (s, 3H); δ6.69 (s, 1H); δ6.98-6.99 (d, 1H); δ7.28 (s, 2H); δ7.41-7.45 (m, 5H); δ8.94 (s, 1H); δ10.61 (s, 1H). MS(TOF) 506.2 (M+).

Example 15 (2E)-N-{2,2,2-trichloro-1-[3-(2-bromophenyl)selenourea]-ethyl}cinnamamide

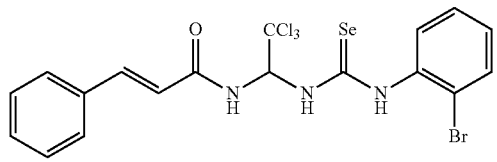

The method of Example 1 was used, except that o-bromoaniline was used in place of p-chloroaniline, to prepare 0.10 g white solid. 1H-NMR (400 MHz, DMSO-d6) δ6.75-6.79 (d, 1H); δ7.23-7.27 (t, 1H); δ7.41-7.45 (m, 5H); δ7.54-7.63 (m, 4H); δ7.69-7.71 (d, 1H); δ8.64 (s, 1H); δ9.07-9.09 (d, 1H); δ10.40 (s, 1H). MS(TOF) 556.1 (M+).

Example 16 (2E)-N-{2,2,2-trichloro-1-[3-(2,3-dimethylphenyl) selenourea]-ethyl}cinnamamide

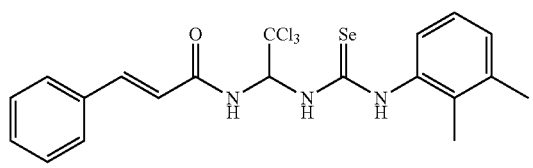

The method of Example 1 was used, except that 2,3-dimethylaniline was used in place of p-chloroaniline, to prepare 0.15 g white solid. 1H-NMR (400 MHz, DMSO-d6) δ2.08 (s, 3H); δ2.28 (s, 3H); δ6.67 (s, 1H); δ7.02-7.04 (d, 1H); δ7.17 (s, 2H); δ7.39-7.46 (m, 3H); δ7.52-7.56 (d, 1H); δ7.61-7.64 (dd, 4H); δ8.96 (s, 1H); δ10.64 (s, 1H). MS(TOF) 503.1 (M+).

Example 17 (2E)-N-[2,2,2-trichloro-1-(3-phenyl selenourea)-ethyl] cinnamamide

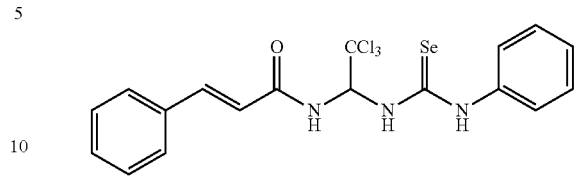

The method of Example 1 was used, except that aniline was used in place of p-chloroaniline, to prepare 0.17 g white solid. 1H-NMR (400 MHz, DMSO-d6) δ6.68-6.72 (d, 1H); 7.26-7.28 (t, 1H); δ7.40-7.46 (m, 7H); δ7.53-7.59 (m, 2H); δ7.61-7.63 (dd, 2H); δ8.30 (s, 1H); δ8.92-8.94 (d, 1H); δ10.79 (s, 1H). MS(TOF) 475.0 (M+).

Example 18 (2E)-N-{2,2,2-trichloro-1-[3-(2-chlorophenyl) selenourea]-ethyl}cinnamamide

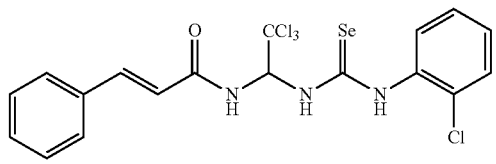

The method of Example 1 was used, except that o-chloroaniline was used in place of p-chloroaniline, to prepare 0.17 g white solid. 1H-NMR (400 MHz, DMSO-d6) δ6.76-6.80 (d, 1H); 7.32-7.46 (m, 5H); δ7.54-7.63 (m, 6H); δ8.66 (s, 1H); δ9.06-9.08 (d, 1H); δ10.43 (s, 1H). MS(TOF) 509.5 (M+).

Example 19 (2E)-N-{2,2,2-trichloro-1-[3-(3-bromophenyl) selenourea]-ethyl}cinnamamide

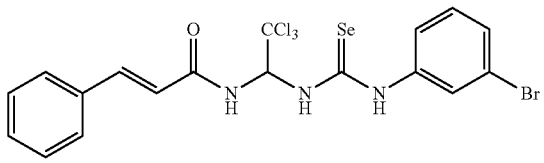

The method of Example 1 was used, except that 3-bromoaniline was used in place of p-chloroaniline, to prepare 0.17 g white solid. 1H-NMR (400 MHz, DMSO-d6) δ6.73-6.77 (d, 1H); 7.36-7.45 (m, 6H); δ7.54-7.64 (m, 4H); δ7.85 (s, 1H); δ8.57-8.59 (d, 1H); δ8.89-8.91 (d, 1H); δ10.84 (s, 1H). MS(TOF) 475.0 (M+).

Example 20 (2E)-N-{2,2,2-trichloro-1-[3-(2-chlorobenzyl) selenourea]-ethyl}cinnamamide

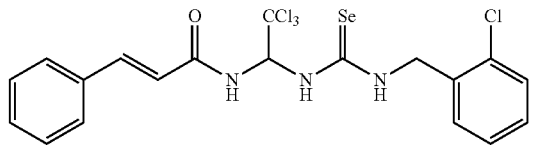

The method of Example 1 was used, except that o-chlorobenzylamine was used in place of p-chloroaniline, to prepare 0.15 g white solid. 1H-NMR (400 MHz, DMSO-d6) δ4.86-4.89 (t, 2H); δ6.78-6.82 (d, 1H); δ7.34-7.37 (m, 2H); δ7.41-7.51 (m, 6H); δ7.53-7.61 (m, 3H); δ8.48-8.50 (d, 1H); δ9.03-9.08 (m, 2H). MS(TOF) 524.1 (M+).

Example 21 (2E)-N-[2,2,2-trichloro-1-(3-isobutyl selenourea)-ethyl] cinnamamide

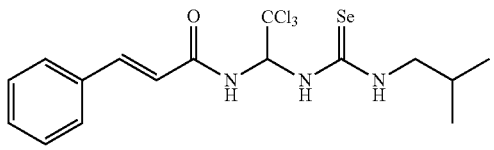

The method of Example 1 was used, except that isobutylamine was used in place of p-chloroaniline, to prepare 0.09 g white solid. 1H-NMR (400 MHz, DMSO-d6) δ0.85-0.91 (d, 6H); 1.86-1.89 (m, 1H); δ3.36-3.38 (m, 2H); δ6.77-6.81 (d, 1H); δ7.42-7.59 (m, 7H); δ8.18-8.21 (d, 1H); δ8.68-8.71 (t, 1H); δ8.90-8.92 (d, 1H). MS(TOF) 455.0 (M+).

Example 22 (2E)-N-{2,2,2-trichloro-1-[3-(4-hydroxyphenyl) selenourea]-ethyl)}cinnamamide

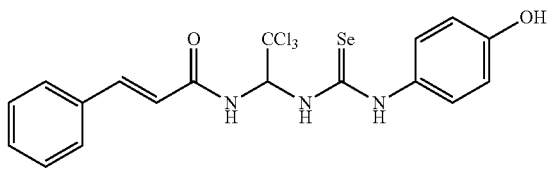

The method of Example 1 was used, except that p-hydroxyaniline was used in place of p-chloroaniline, to prepare 0.15 g white solid. 1H-NMR (400 MHz, DMSO-d6) δ5.59-5.62 (d, 1H); 5.78 (s, 1H); δ5.97-5.99 (m, 7H); δ6.58-6.60 (d, 2H); δ6.69-6.71 (d, 2H); δ6.78-6.82 (d, 1H); δ7.39-7.44 (m, 3H); δ7.51-7.59 (m, 3H); δ8.71 (s, 1H); δ8.81-8.83 (d, 1H). MS(TOF) 491.0 (M+).

Example 23 (2E)-N-{2,2,2-trichloro-1-[3-(4-bromophenyl) selenourea]-ethyl)}cinnamamide

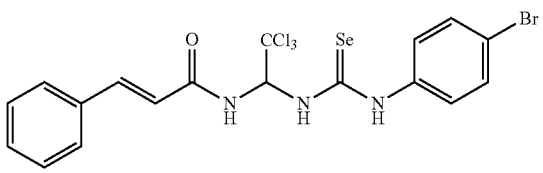

The method of Example 1 was used, except that p-bromoaniline was used in place of p-chloroaniline, to prepare 0.13 g white solid. 1H-NMR (400 MHz, DMSO-d6) δ6.72-6.76 (d, 1H); 7.41-7.64 (m, 11H); δ8.48-8.50 (d, 1H); δ8.92-8.94 (d, 1H); δ10.79 (s, 1H). MS(TOF) 553.9 (M+).

Example 24 (2E)-N-[3-methyl-1-(3-phenyl thioureido) butyl]-3-(3,4,5-trimethoxyphenyl) acrylamide

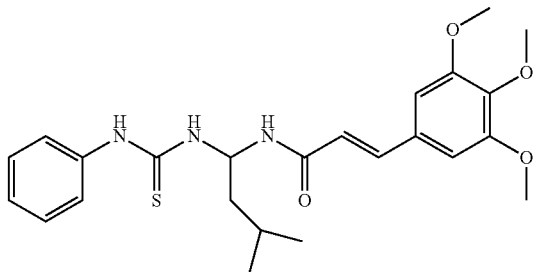 [SMILES: COc1cc(/C=C/C(=O)NC(CC(C)C)NC(=S)Nc2ccccc2)cc(OC)c1OC]

100 g 3,4,5-trimethoxyphenylaldehyde, and 64.5 g malonic acid were weighted and placed in a three-necked bottle, and 500 ml pyridine and 10 ml piperidine were added. The reaction was carried out at 80° C. under reflux for 24 h and then stopped, pH of the reaction system was adjusted to 12 by using NaOH. The solution was extracted with water, acetic ether for three times, and the water phase was collected and adjusted to a pH of 3. White solids were precipitated, filtered and infra-red dried to prepare 93 g solid 3-(3,4,5-trimethoxyphenyl) acrylic acid. 2.4 g 3-(3,4,5-trimethoxyphenyl) acrylic acid, 3.1 g p-toluene sulfonyl chloride, 4.0 g potassium carbonate, and 5.2 g tetramethylammonium chloride were weighted and placed in a 50 ml round bottom flask, and 30 ml DCM was added. The reaction was carried out at 40° C. for 1 h and then stopped. Inorganic salts were removed by filtration, and the solution was dried under rotation. The residue was dissolved in methanol and filtered to prepare 2.73 g 3-(3,4,5-trimethoxyphenyl) acrylic acid p-toluenesulfonate. 2.7 g 3-(3,4,5-trimethoxyphenyl) acrylic acid p-toluenesulfonate was weighted and added to a 100 ml round bottom flask, and 40 ml DCM, 2 ml DIEA, and 20 ml concentrated ammonia water were added dropwise. After the addition, the temperature was increased to 40° C., and the reaction was stopped 2 h later. Insoluble substances were removed by filtration, and the resultant solution was dried under rotation, and was recrystallized in acetic ether to prepare 1 g of the compound 3-(3,4,5-trimethoxyphenyl) acrylamide. 4 g benzotriazole, 2 ml isovaleraldehyde, and 2 g 3-(3,4,5-trimethoxyphenyl) acrylamide were weighted and added to a three-necked bottle, followed by the addition of 20 ml toluene, and the dropwise addition of three drops of concentrated HCl. The reaction was carried out under reflux for 10 h, and then stopped. Toluene was evaporated under rotation. Chromotographic purification was carried out through silica gel column to prepare 1 g N-(1-benzotriazol-1-yl-3-methyl-butyl]-3-(3,4,5-trimethoxyphenyl)acrylamide. 930 mg aniline, 880 mg CS$_2$, and 880 mg KOH were added to a 100 ml three-necked bottle, followed by the addition of 20 ml DMSO. The reaction was carried out at 30° C. for 12 h, and then cooled, 1420 g ICH$_3$ was added, and the reaction was carried out in an ice bath for 15 h and then stopped. The reaction solution was slowly added dropwise to water to precipitate solids. Chromotographic purification was carried out through silica gel column to prepare 500 mg white solid methyl N-phenyl dithiocarbamate. 500 mg white solid methyl N-phenyl dithiocarbamate was weighted and added to a round bottom flask, followed by the addition of 20 ml methanol and 2.5 ml ammonia water. The reaction was carried out under reflux for 2 h and then stopped. Methanol was evaporated under rotation, and 200 mg solid phenylthiocarbamide was precipitated. 270 mg solid K phenylthiocarbamide and 150 mg NaH were placed in a reaction bottle, followed by the addition of 6 ml THF. After the reaction at room temperature for 1 h, 720 mg N-(1-benzotriazol-1-yl-3-methyl-butyl]-3-(3,4,5-trimethoxyphenyl) acrylamide was dissolved in 4 ml THF, and the resultant solution was added to the reaction bottle. The reaction was carried out at room temperature for 3 h and then stopped. The solution was washed with acetic ether/water for three times, washed with saturated saline twice, and dried with anhydrous sodium sulphate. The solvent was evaporated under rotation. Chromotographic purification was carried out through silica gel column to prepare 200 mg solid. 1H-NMR (400 MHz, DMSO-d6) δ0.90-0.94 (m, 6H); δ1.48-1.71 (m, 4H); δ3.68 (s, 2H); δ3.80 (s, 6H); δ6.48-6.52 (d, 2H); δ6.86 (s, 2H); δ7.02 (s, 1H); δ7.38-7.48 (m, 4H); δ8.08 (s, 1H). MS(TOF) 457.6 (M+).

Example 25 (2E)-N-[3-methyl-1-(3-pyridin-3-yl thioureido) butyl]-3-(3,4,5-trimethoxyphenyl) acrylamide

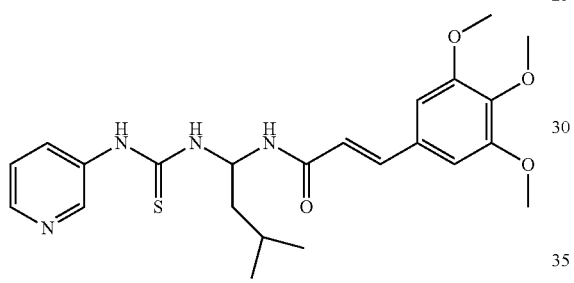

The method of Example 24 was used, except that 3-amino-pyridine was used in place of aniline, to prepare 210 mg the compound. 1H-NMR (400 MHz, CCl3D-d) 60.94 (s, 6H); δ1.71-1.78 (m, 3H); δ3.80 (m, 1H); δ3.87-3.89 (s, 10H); δ5.66 (s, 1H); δ6.39-6.43 (d, 1H); δ6.75 (s, 2H); δ6.92-6.94 (d, 1H); δ7.30-7.33 (m, 1H); δ7.65-7.67 (d, 1H); δ8.21-8.23 (d, 1H); δ8.41-8.42 (d, 1H); δ8.82 (s, 1H); δ10.95 (s, 1H). MS(TOF) 458.6 (M+).

Example 26 (2E)-N-[3,3-dimethyl-1-(3-phenyl thioureido) propyl]-3-(3,4,5-trimethoxyphenyl) acrylamide

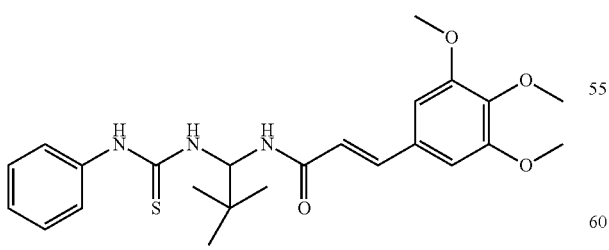

The method of Example 24 was used, except that pivaldehyde was used in place of isovaleraldehyde, to prepare 150 mg the compound. 1H-NMR (400 MHz, DMSO-d6) δ0.92-1.01 (s, 9H); δ1.76 (m, 1H); δ3.69 (s, 3H); δ3.82 (s, 6H); δ6.05 (d, 1H); δ6.57-6.59 (m, 1H); δ6.91 (d, 2H); δ7.10-7.13 (m, 1H); δ7.30-7.35 (m, 2H); δ7.48 (s, 1H); δ7.93 (s, 1H); δ8.55 (d, 1H); δ8.82 (s, 1H); δ9.70 (s, 1H). MS(TOF) 458.6 (M+).

Example 27 (2E)-N-[2,2-dimethyl-1-(3-pyridin-3-yl thioureido) propyl]-3-(3,4,5-trimethoxyphenyl) acrylamide

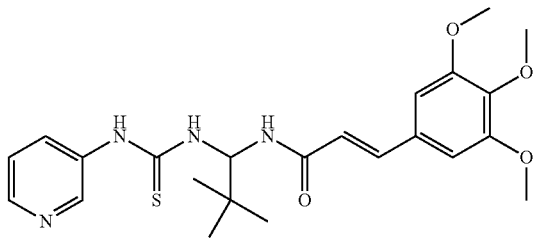 [SMILES: COc1cc(/C=C/C(=O)NC(NC(=S)Nc2cccnc2)C(C)(C)C)cc(OC)c1OC]

The method of Example 24 was used, except that 3-aminopyridine was used in place of aniline, pivaldehyde was used in place of isovaleraldehyde, to prepare 230 mg the compound. 1H-NMR (400 MHz, CCl3D-d) δ0.90-1.15 (s, 9H); δ3.84-3.90 (s, 9H); δ5.42 (m, 1H); δ6.44-6.46 (m, 1H); δ6.49-6.53 (d, 1H); δ6.64-6.66 (d, 1H); δ6.78 (s, 2H); δ7.29-7.32 (t, 1H); δ7.69-7.73 (d, 1H); δ8.26-8.42 (d, 1H); δ8.42-8.43 (d, 1H); δ8.74-8.75 (d, 1H); δ10.55 (s, 1H). MS(TOF) 458.6 (M+).

Example 28 (2E)-N-[cyclopropyl-(3-phenyl thioureido)-methyl]-3-(3,4,5-trimethoxyphenyl) acrylamide

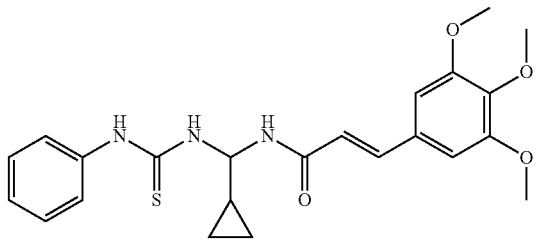 [SMILES: COc1cc(/C=C/C(=O)NC(NC(=S)Nc2ccccc2)C2CC2)cc(OC)c1OC]

The method of Example 24 was used, except that cyclopropanecarboxaldehyde was used in place of isovaleraldehyde, to prepare 250 mg the compound. 1H-NMR (400 MHz, DMSO-d6) δ0.91 (m, 1H); δ2.05-2.07 (m, 2H); δ3.75 (s, 4H); δ3.79-3.80 (m, 2H); δ3.88 (s, 6H); δ6.03 (m, 1H); δ6.71-6.75 (d, 1H); δ7.03 (s, 2H); δ7.16-7.22 (m, 1H); δ7.36-7.40 (t, 2H); δ7.59-7.61 (d, 2H); δ9.24 (s, 1H); δ10.60 (s, 1H). MS(TOF) 441.5 (M+).

Example 29 (2E)-N-[cyclopropyl-(3-pyridin-3-yl thioureido)-methyl]-3-(3,4,5-trimethoxyphenyl) acrylamide

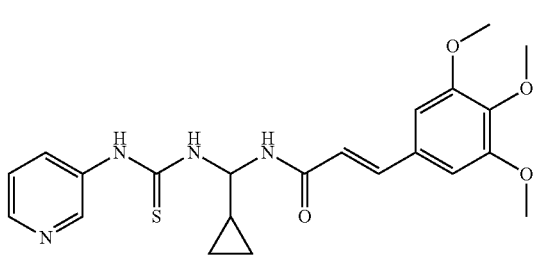 [SMILES: COc1cc(/C=C/C(=O)NC(NC(=S)Nc2cccnc2)C2CC2)cc(OC)c1OC]

The method of Example 24 was used, except that 3-aminopyridine was used in place of aniline, cyclopropanecarboxaldehyde was used in place of isovaleraldehyde, to prepare 210 mg the compound. 1H-NMR (400 MHz, CCl3D-d) 80.51-0.57 (m, 4H); δ1.25-1.26 (m, 1H); δ2.45 (s, 1H); δ3.87 (s, 9H); δ4.99 (s, 1H); δ6.43-6.47 (d, 1H); δ6.74 (s, 1H); δ7.27-7.31 (m, 2H); δ7.41-7.43 (d, 1H); δ7.63-7.67 (d, 1H); δ8.18 (s, 2H); δ8.39-8.40 (d, 1H); δ8.79 (s, 1H); δ10.78 (s, 1H). MS(TOF) 442.5 (M+).

Example 30 (2E)-N-[cyclopropyl-(3-pyridin-2-yl thioureido)-methyl]-3-(3,4,5-trimethoxyphenyl) acrylamide

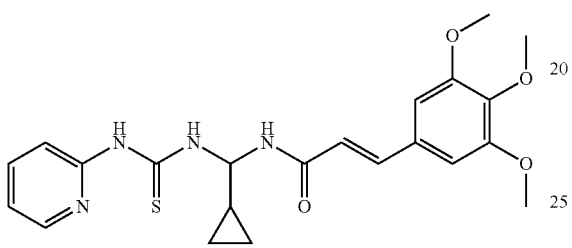

The method of Example 24 was used, except that 2-aminopyridine was used in place of aniline, cyclopropanecarboxaldehyde was used in place of isovaleraldehyde, to prepare 170 mg the compound. 1H-NMR (400 MHz, DMSO-d6) δ0.45-0.50 (m, 4H); δ1.45-1.47 (m, 1H); δ3.68 (s, 3H); δ3.81 (s, 6H); δ5.92-5.94 (m, 1H); δ6.55-6.59 (d, 1H); δ6.91 (s, 1H); δ7.06-7.09 (dd, 1H); δ7.17-7.19 (d, 1H); δ7.37-7.41 (d, 1H); δ7.79-7.80 (t, 1H); δ8.61-8.63 (d, 1H); δ10.66 (s, 1H); δ12.17-12.19 (d, 1H). MS(TOF) 442.5 (M+).

Example 31 (2E)-N-[3-methyl-1-(3-pyridin-2-yl thioureido)butyl]-3-(3,4,5-trimethoxyphenyl) acrylamide

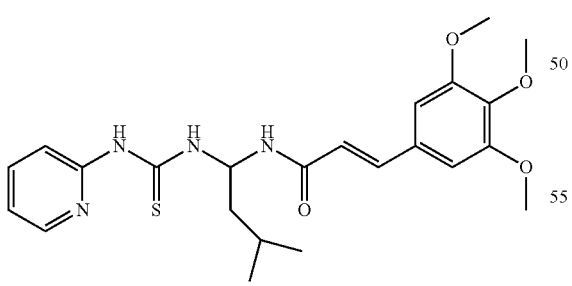

The method of Example 24 was used, except that 2-aminopyridine was used in place of aniline, to prepare 210 mg the compound. 1H-NMR (400 MHz, CCl3D-d) δ1.00-1.01 (s, 6H); δ1.73-1.76 (m, 2H); δ2.16 (s, 2H); δ3.87 (s, 9H); δ5.88 (s, 1H); δ6.32-6.36 (d, 1H); δ6.71-6.76 (m, 3H); δ6.98-7.00 (m, 1H); δ7.09 (m, 1H); δ7.51-7.55 (d, 1H); δ7.64 (m, 1H); δ8.24-8.25 (m, 1H); δ10.32 (s, 1H). MS(TOF) 458.6 (M+).

Example 32 (2E)-N-[3,3-dimethyl-1-(3-phenyl thioureido)butyl]-3-(3,4,5-trimethoxyphenyl)acrylamide

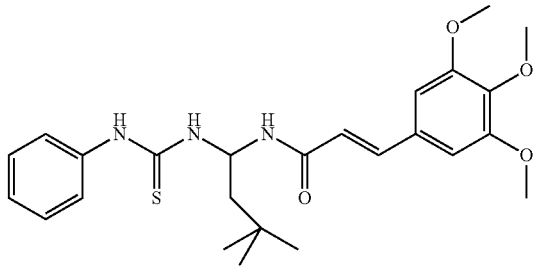 [SMILES: COc1cc(/C=C/C(=O)NC(CC(C)(C)C)NC(=S)Nc2ccccc2)cc(OC)c1OC]

The method of Example 24 was used, except that 3,3-dimethyl butyraldehyde was used in place of isovaleraldehyde, to prepare 170 mg the compound.
1H-NMR (400 MHz, DMSO-d6) δ0.92-0.99 (m, 9H); δ1.78 (s, 2H); δ3.68 (s, 3H); δ3.81 (s, 6H); δ6.06 (m, 1H); δ6.57-6.59 (d, 1H); δ6.91 (s, 2H); δ7.09-7.13 (m, 1H); δ7.31-7.35 (m, 5H); δ7.92 (s, 1H); δ68.55 (s, 1H); δ9.70 (s, 1H); MS(TOF) 471.6 (M+).

Example 33 (2E)-N-[3,3-dimethyl-1-(3-pyridin-3-yl thioureido)butyl]-3-(3,4,5-trimethoxyphenyl) acrylamide

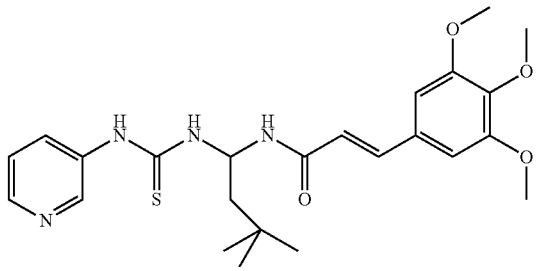 [SMILES: COc1cc(/C=C/C(=O)NC(CC(C)(C)C)NC(=S)Nc2cccnc2)cc(OC)c1OC]

The method of Example 24 was used, except that 3-aminopyridine was used in place of aniline, 3,3-dimethylbutyraldehyde was used in place of isovaleraldehyde, to prepare 160 mg the compound. 1H-NMR (400 MHz, CCl3D-d) 61.01 (s, 9H); δ1.79-1.82 (m, 1H); δ2.05 (m, 2H); δ3.89 (s, 9H); δ5.71 (s, 1H); δ6.37-6.41 (d, 1H); δ6.76 (m, 2H); δ7.15 (m, 1H); δ7.31-7.34 (m, 1H); δ7.67-7.71 (d, 1H); δ8.24-8.26 (d, 1H); δ8.42-8.43 (d, 1H); δ8.83 (s, 1H); δ10.92 (s, 1H). MS(TOF) 472.6 (M+).

Example 34 (2E)-N-[3,3-dimethyl-1-(3-pyridin-2-yl thioureido)butyl]-3-(3,4,5-trimethoxyphenyl) acrylamide

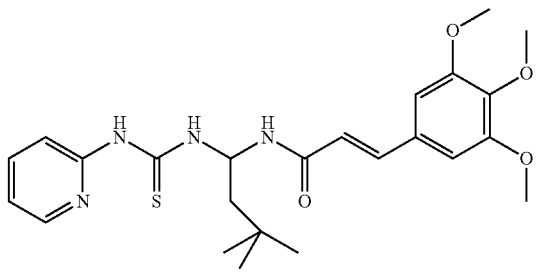 [SMILES: COc1cc(/C=C/C(=O)NC(CC(C)(C)C)NC(=S)Nc2ccccn2)cc(OC)c1OC]

The method of Example 24 was used, except that 2-aminopyridine was used in place of aniline, 3,3-dimethylbutyraldehyde was used in place of isovaleraldehyde, to prepare 170 mg the compound. 1H-NMR (400 MHz, CCl3D-d) δ1.02 (s, 9H); δ1.74 (s, 1H); δ2.17-2.31 (m, 2H); δ3.87 (s, 9H); δ5.90 (s, 1H); δ6.30-6.34 (d, 1H); δ6.70-6.77 (m, 3H); δ6.98-7.00 (m, 1H); δ7.17 (s, 1H); δ7.50-7.54 (d, 1H); δ7.64 (m, 1H); δ8.25-8.26 (d, 1H); δ8.43 (s, 1H); δ12.39 (s, 1H). MS(TOF) 458.6 (M+).

Example 35 (2E)-N-[2-methyl-1-(3-pyridin-2-yl thioureido)propyl]-3-(3,4,5-trimethoxyphenyl) acrylamide

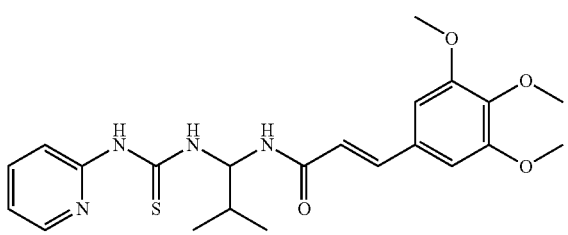 [SMILES: COc1cc(/C=C/C(=O)NC(NC(=S)Nc2ccccn2)C(C)C)cc(OC)c1OC]

The method of Example 24 was used, except that 2-aminopyridine was used in place of aniline, isobutyraldehyde was used in place of isovaleraldehyde, to prepare 170 mg the compound. 1H-NMR (400 MHz, DMSO-d6) δ0.95-0.99 (m, 6H); δ2.21-2.24 (m, 1H); δ3.68 (s, 3H); δ3.81 (s, 6H); δ6.02-6.04 (m, 1H); δ6.61-6.64 (d, 1H); δ6.90 (s, 2H); δ7.08-7.12 (m, 1H); δ7.18-7.20 (m, 1H); δ7.36-7.40 (d, 5H); δ7.78-7.80 (m, 1H); δ8.24-8.25 (m, 1H); δ8.50-8.52 (m, 1H); δ10.70 (s, 1H); δ12.16-12.18 (d, 1H); MS(TOF) 428.5 (M+).

Example 36 (2E)-N-[2-methyl-1-(3-phenyl thioureido)propyl]-3-(3,4,5-trimethoxyphenyl) acrylamide

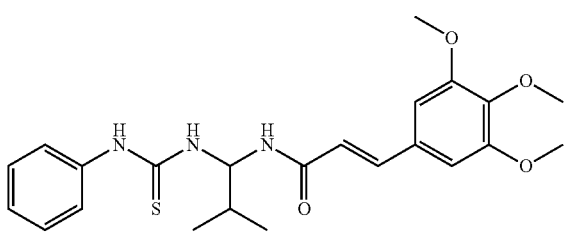 [SMILES: COc1cc(/C=C/C(=O)NC(NC(=S)Nc2ccccc2)C(C)C)cc(OC)c1OC]

The method of Example 24 was used, except that isobutyraldehyde was used in place of isovaleraldehyde, to prepare 170 mg the compound. 1H-NMR (400 MHz, DMSO-d6) δ0.93-0.95 (m, 6H); δ2.20 (m, 1H); δ3.69 (s, 3H); δ3.82 (s, 6H); δ5.86 (m, 1H); δ6.78-6.80 (d, 1H); δ6.92 (s, 2H); δ7.11-7.13 (m, 1H); δ7.30-7.54 (m, 6H); δ7.97 (s, 1H); δ8.30 (m, 1H); δ9.91 (m, 1H); MS(TOF) 428.5 (M+).

Example 37 (2E)-N-[cyclopropyl-(3-pyridin-2-yl thioureido)-methyl] cinnamamide

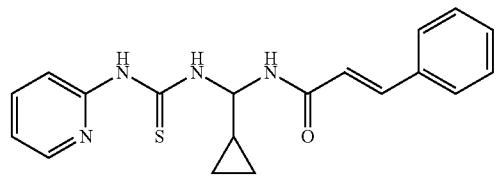 [SMILES: O=C(/C=C/c1ccccc1)NC(NC(=S)Nc1ccccn1)C1CC1]

The method of Example 24 was used, except that 2-aminopyridine was used in place of aniline, cyclopropanecarboxaldehyde was used in place of isovaleraldehyde, phenylaldehyde was used in place of 3,4,5-trimethoxyphenylaldehyde, to prepare 170 mg the compound. 1H-NMR (400 MHz, DMSO-d6) δ0.93-0.95 (m, 6H); δ1.91-2.29 (m, 4H); δ3.68-3.71 (m, 1H); δ3.82 (s, 6H); δ6.62-6.65 (m, 1H); δ7.00-7.53 (m, 8H); δ7.70-7.80 (m, 3H); δ8.23-8.24 (m, 1H); δ10.86-10.87 (m, 1H); δ12.47-12.49 (m, 1H); MS(TOF) 352.5 (M+).

Example 38 (2E)-N-[3-methyl-1-(3-phenyl thioureido)butyl] cinnamamide

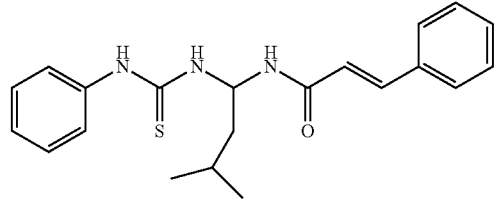 [SMILES: CC(C)CC(NC(=O)/C=C/c1ccccc1)NC(=S)Nc1ccccc1]

The method of Example 24 was used, except that phenylaldehyde was used in place of 3,4,5-trimethoxyphenylaldehyde, to prepare 180 mg the compound. 1H-NMR (400 MHz, DMSO-d6) δ0.91-0.92 (m, 6H); δ1.67-1.73 (m, 3H); δ6.03 (s, 1H); δ6.66 (s, 1H); δ7.10-7.13 (t, 1H); δ7.30-7.60 (m, 10H); δ7.96 (s, 1H); δ8.56 (s, 1H); δ9.67 (s, 1H); MS(TOF) 367.5 (M+).

Example 39 (2E)-N-[3,3-dimethyl-1-(3-phenyl thioureido)butyl] cinnamamide

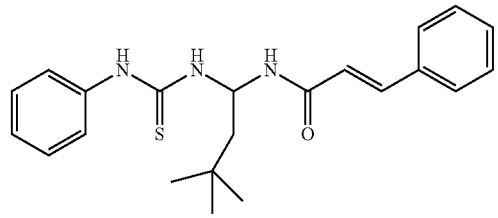 [SMILES: CC(C)(C)CC(NC(=O)/C=C/c1ccccc1)NC(=S)Nc1ccccc1]

The method of Example 24 was used, except that 3,3-dimethyl butyraldehyde was used in place of isovaleraldehyde, phenylaldehyde was used in place of 3,4,5-trimethoxyphenylaldehyde, to prepare 170 mg the compound. 1H-NMR (400 MHz, DMSO-d6) δ0.92-0.95 (m, 9H); δ1.78 (m, 2H); δ6.06 (s, 1H); δ6.60-6.64 (d, 1H);

δ7.10-7.13 (t, 1H); δ7.31-7.57 (m, 10H); δ7.97 (s, 1H); δ8.65 (s, 1H); δ9.71 (s, 1H). MS(TOF) 381.5 (M+).

Example 40 (2E)-N-[2,2-dimethyl-1-(3-phenyl thioureido)propyl] cinnamamide

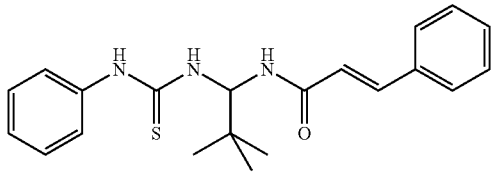 [SMILES: CC(C)(C)C(NC(=O)/C=C/c1ccccc1)NC(=S)Nc1ccccc1]

The method of Example 24 was used, except that 3,3-dimethyl propylaldehyde was used in place of isovaleraldehyde, phenylaldehyde was used in place of 3,4,5-trimethoxyphenylaldehyde. 1H-NMR (400 MHz, DMSO-d6) δ0.98 (m, 9H); δ6.15 (s, 1H); δ6.69-6.72 (d, 1H); δ7.11-7.15 (t, 1H); δ7.32-7.59 (m, 10H); δ7.63-7.67 (d, 1H); δ8.17 (s, 1H); δ9.86 (s, 1H). MS(TOF) 367.5 (M+).

Example 41 (2E)-N-[cyclopropyl-(3-phenyl thioureido)cyclopropyl methyl]cinnamamide

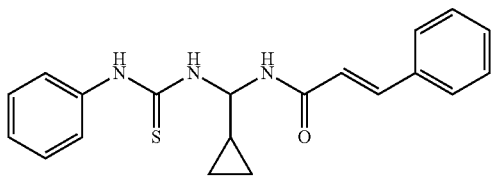 [SMILES: O=C(/C=C/c1ccccc1)NC(NC(=S)Nc1ccccc1)C1CC1]

The method of Example 24 was used, except that cyclopropanecarboxaldehyde was used in place of isovaleraldehyde, phenylaldehyde was used in place of 3,4,5-trimethoxyphenylaldehyde, to prepare 170 mg the compound. 1H-NMR (400 MHz, DMSO-d6) δ1.89-2.19 (m, 4H); δ3.57-3.58 (m, 1H); δ6.58-6.62 (t, 1H); δ7.07-7.11 (t, 1H); δ7.20-7.54 (m, 10H); δ7.69-7.71 (dd, 2H); δ9.11 (d, 1H); δ10.01 (s, 1H). MS(TOF) 351.5 (M+).

Example 42 (2E)-N-[2-methyl-1-(3-phenyl thioureido)propyl] cinnamamide

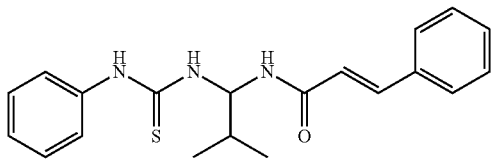 [SMILES: CC(C)C(NC(=O)/C=C/c1ccccc1)NC(=S)Nc1ccccc1]

The method of Example 24 was used, except that isobutyraldehyde was used in place of isovaleraldehyde, phenylaldehyde was used in place of 3,4,5-trimethoxyphenylaldehyde, to prepare 170 mg the compound. 1H-NMR (400 MHz, DMSO-d6) δ0.92-0.94 (m, 6H); δ2.22 (s, 1H); δ5.83 (s, 1H); δ6.70 (d, 1H); δ7.09-7.13 (t, 1H); δ7.31-7.58 (m, 10H); δ7.85 (s, 1H); δ8.43 (s, 1H); δ9.77 (s, 1H). MS(TOF) 353.5 (M+).

Example 43 (2E)-N-[3-methyl-1-(3-methyl thioureido) butyl]-3-(3,4,5-trimethoxyphenyl) acrylamide

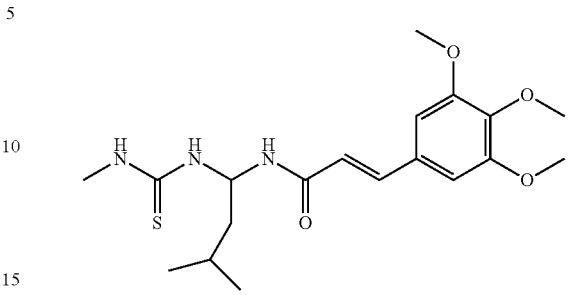

The method of Example 24 was used, except that methylamine was used in place of aniline, to prepare 190 mg the compound. 1H-NMR (400 MHz, DMSO-d6) δ0.94-0.97 (m, 7H); δ1.66-1.70 (m, 3H); δ2.93 (s, 3H); δ3.75 (s, 3H); δ3.78 (s, 6H); δ5.95-5.99 (d, 1H); δ6.64-6.68 (d, 1H); δ6.97 (s, 2H); δ7.47-7.52 (d, 1H); δ8.01 (s, 1H); δ8.74 (t, 1H). MS(TOF) 442.5 (M+).

Example 44 (2E)-N-[2,2-dimethyl-1-(3-o-methyl phenyl thioureido) propyl]-3-(3,4,5-trimethoxyphenyl)acrylamide

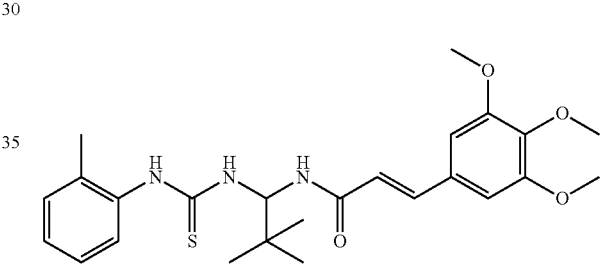

The method of Example 24 was used, except that 2-methylaniline was used in place of aniline, pivaldehyde was used in place of isovaleraldehyde, to prepare 170 mg the compound. 1H-NMR (400 MHz, DMSO-d6) δ0.94 (m, 9H); δ2.19 (s, 3H); δ3.68 (s, 3H); δ3.81 (s, 6H); δ6.19 (s, 1H); δ6.61-6.65 (d, 1H); δ6.92 (s, 2H); δ7.16-7.52 (m, 6H); δ8.61 (d, 1H); δ9.46 (s, 1H). MS(TOF) 471.6 (M+).

Example 45 (2E)-N-[cyclopropyl-(3-o-methyl phenyl thioureido)-methyl]-3-(3,4,5-trimethoxyphenyl) acrylamide

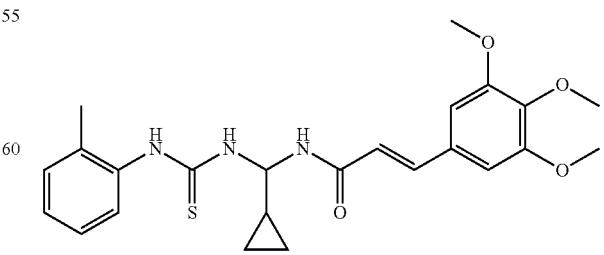

The method of Example 24 was used, except that 2-methylaniline was used in place of aniline, cyclopropanecarboxaldehyde was used in place of isovaleraldehyde, to prepare 170 mg the compound. 1H-NMR (400 MHz, DMSO-d6) δ0.38-0.46 (m, 4H); δ1.42 (s, 1H); δ2.18 (s, 3H); δ3.68 (s, 3H); δ3.81 (s, 6H); δ5.72 (s, 1H); δ6.57-6.63 (d, 1H); δ6.92 (s, 2H); δ7.14-7.40 (m, 5H); δ7.76 (s, 1H); δ8.36 (s, 1H); δ9.346 (s, 1H). MS(TOF) 455.6 (M+).

Example 46 N-[3,3-dimethyl-1-(3-o-methyl phenyl thioureido) butyl] cinnamamide

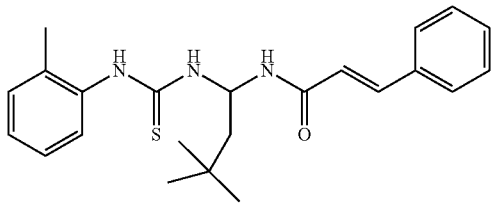 [SMILES: Cc1ccccc1NC(=S)NC(CC(C)(C)C)NC(=O)/C=C/c1ccccc1]

The method of Example 24 was used, except that 2-methylaniline was used in place of aniline, 3, 3-dimethylbutyraldehyde was used in place of isovaleraldehyde, phenylaldehyde was used in place of 3,4,5-trimethoxyphenylaldehyde, to prepare 170 mg the compound. 1H-NMR (400 MHz, DMSO-d6) δ0.95 (m, 9H); δ1.69-1.80 (m, 2H); δ2.16 (s, 3H); δ6.06 (s, 1H); δ6.59-6.63 (d, 1H); δ7.13-7.24 (m, 4H); δ7.41-7.44 (m, 4H); δ7.57-7.59 (d, 3H); δ8.59 (s, 1H); δ9.24 (s, 1H). MS(TOF) 395.6 (M+).

Example 47 N-[3-methyl-1-(3-o-methyl phenyl thioureido)butyl] cinnamamide

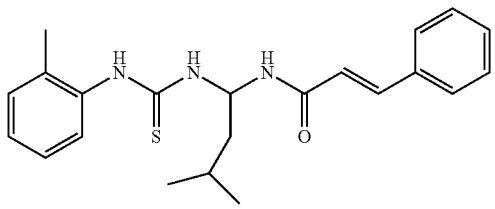 [SMILES: Cc1ccccc1NC(=S)NC(CC(C)C)NC(=O)/C=C/c1ccccc1]

The method of Example 24 was used, except that 2-methylaniline was used in place of aniline, phenylaldehyde was used in place of 3,4,5-trimethoxyphenylaldehyde, to prepare 170 mg the compound. 1H-NMR (400 MHz, DMSO-d6) δ0.86-0.92 (m, 6H); δ1.24-1.25 (m, 1H); δ1.67-1.68 (m, 2H); δ2.16 (s, 3H); δ6.05 (s, 1H); δ5.47-5.52 (s, 1H, N—H); δ6.06 (s, 1H); δ6.64-6.69 (m, 1H); δ7.15-7.18 (m, 4H); δ7.41-7.43 (m, 3H); δ7.58-7.59 (d, 2H); δ8.47 (s, 1H); δ9.20 (s, 1H) 69.95 (s, 1H, N—H); MS(TOF) 381.5 (M+).

Example 48 N-[2,2-dimethyl-1-(3-o-methyl phenyl thioureido) propyl] cinnamamide

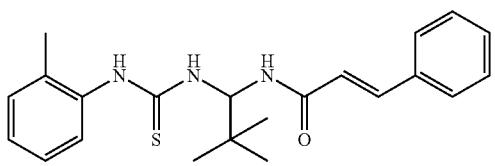 [SMILES: Cc1ccccc1NC(=S)NC(NC(=O)/C=C/c1ccccc1)C(C)(C)C]

The method of Example 24 was used, except that 2-methylaniline was used in place of aniline, pivaldehyde was used in place of isovaleraldehyde, phenylaldehyde was used in place of 3,4,5-trimethoxyphenylaldehyde, to prepare 170 mg the compound. 1H-NMR (400 MHz, DMSO-d6) δ0.94 (m, 9H); δ2.18 (s, 3H); δ6.15 (s, 1H); δ6.71 (s, 1H); δ7.17-7.26 (m, 4H); δ7.38-7.45 (m, 4H); δ7.57-7.59 (d, 2H); δ8.19 (s, 1H). MS(TOF) 381.5 (M+).

Example 49 N-[cyclopropyl-(3-o-methyl phenyl thioureido)-methyl] cinnamamide

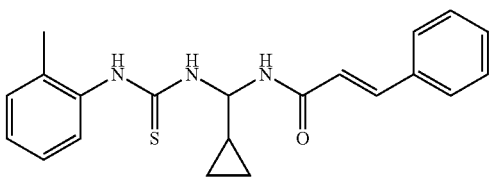 [SMILES: Cc1ccccc1NC(=S)NC(NC(=O)/C=C/c1ccccc1)C1CC1]

The method of Example 24 was used, except that 2-methylaniline was used in place of aniline, cyclopropanecarboxaldehyde was used in place of isovaleraldehyde, phenylaldehyde was used in place of 3,4,5-trimethoxy phenylaldehyde, to prepare 170 mg the compound. 1H-NMR (400 MHz, DMSO-d6) δ1.93-1.95 (m, 2H); δ2.08 (s, 3H); δ2.30 (m, 1H); δ3.71-3.73 (m, 2H); δ5.90 (s, 1H); δ6.66-6.70 (s, 1H); δ7.10-7.20 (m, 4H); δ7.38-7.57 (m, 6H); δ9.16 (s, 1H); δ9.66 (s, 1H). MS(TOF) 365.5 (M+).

Example 50 (2E)-N-{1-[3-(4-methoxyphenyl) thioureido]-2-methyl propyl}-3-(3,4,5-trimethoxyphenyl) acrylamide

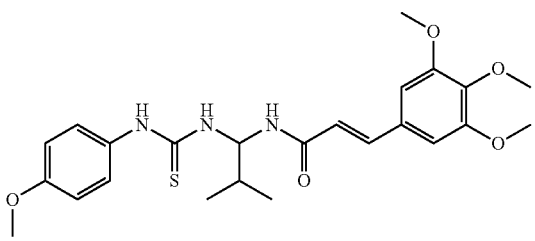 [SMILES: COc1ccc(NC(=S)NC(NC(=O)/C=C/c2cc(OC)c(OC)c(OC)c2)C(C)C)cc1]

The method of Example 24 was used, except that 4-methoxyaniline was used in place of aniline, isobutyraldehyde was used in place of isovaleraldehyde, to prepare 170 mg the compound. 1H-NMR (400 MHz, DMSO-d6) δ0.91-0.98 (m, 6H); δ2.18 (s, 1H); δ3.68 (s, 3H); δ3.74 (s, 3H); δ3.81 (s, 6H); δ5.86 (s, 1H); δ6.60-6.64 (d, 1H); δ6.90-6.92 (d, 2H); δ7.32-7.38 (m, 3H); δ8.30 (s, 1H); δ9.60 (s, 1H). MS(TOF) 473.6 (M+).

Example 51 (2E)-N-[1-(3-cyclohexyl thioureido)-3-methylbutyl]-3-(3,4,5-trimethoxyphenyl) acrylamide

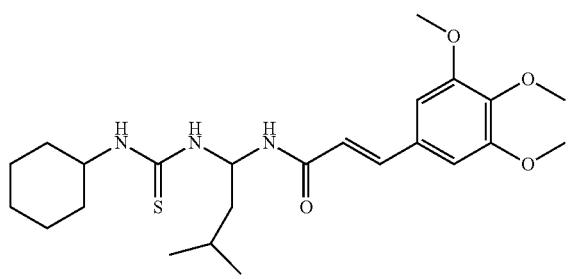 [SMILES: COc1cc(/C=C/C(=O)NC(CC(C)C)NC(=S)NC2CCCCC2)cc(OC)c1OC]

The method of Example 24 was used, except that cyclohexylamine was used in place of aniline, to prepare 170 mg the compound. 1H-NMR (400 MHz, CCl3D-d) δ0.90-0.93 (m, 6H); δ1.29-1.35 (m, 5H); δ1.61-1.77 (m, 5H); δ1.92-2.15 (m, 2H); δ3.89 (m, 9H); δ4.09-4.11 (m, 1H); δ5.44-5.48 (m, 1H); δ6.19 (s, 1H); δ6.47-6.51 (d, 1H); δ6.76-6.85 (m, 2H); δ7.27-7.34 (d, 1H); δ7.57-7.61 (d, 1H); δ8.27 (s, 1H). MS(TOF) 463.6 (M+).

Example 52 (2E)-N-[1-(3-cyclohexyl thioureido)-2,2-dimethylpropyl]-3-(3,4,5-trimethoxyphenyl) acrylamide

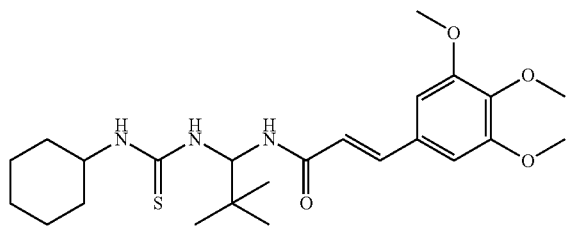 [SMILES: COc1cc(/C=C/C(=O)NC(NC(=S)NC2CCCCC2)C(C)(C)C)cc(OC)c1OC]

The method of Example 24 was used, except that cyclohexylamine was used in place of aniline, pivaldehyde was used in place of isovaleraldehyde, to prepare 170 mg the compound. 1H-NMR (400 MHz, CCl3D-d) δ1.02-1.28 (m, 13H); δ1.68-2.10 (m, 6H); δ3.87-3.95 (M, 9H) δ4.11-4.14 (M, 1H); δ5.21-5.23 (t, 1H); δ6.01-6.03 (d, 1H); δ6.67-6.61 (m, 1H); δ6.75-6.80 (m, 2H); δ7.58-7.62 (m, 1H); δ7.72-7.74 (d, 1H). MS(TOF) 463.6 (M+).

Example 53 (2E)-N-[1-(3-cyclohexyl thioureido)-2-methylpropyl]-3-(3,4,5-trimethoxyphenyl) acrylamide

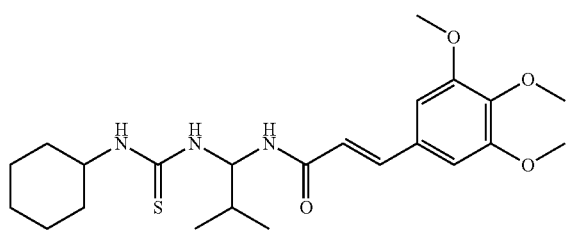 [SMILES: COc1cc(/C=C/C(=O)NC(NC(=S)NC2CCCCC2)C(C)C)cc(OC)c1OC]

The method of Example 24 was used, except that cyclohexylamine was used in place of aniline, isobutyraldehyde was used in place of isovaleraldehyde, to prepare 170 mg the compound. 1H-NMR (400 MHz, -d) δ1.02-1.34 (m, 11H); δ1.63-2.05 (m, 6H); δ3.87-3.89 (m, 9H); δ4.09-4.11 (m, 1H); δ5.14-5.18 (m, 1H); δ6.17 (s, 1H); δ6.55-6.59 (d, 1H); δ6.74-6.78 (m, 2H); δ7.57-7.61 (d, 1H); δ8.02 (s, 1H). MS(TOF) 449.6 (M+).

Example 54 N-[1-(3-cyclohexyl thioureido)-3-methylbutyl] cinnamamide

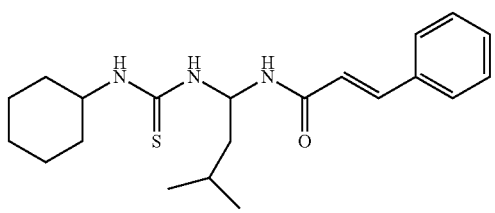 [SMILES: CC(C)CC(NC(=O)/C=C/c1ccccc1)NC(=S)NC1CCCCC1]

The method of Example 24 was used, except that cyclohexylamine was used in place of aniline, phenylaldehyde was used in place of 3,4,5-trimethoxyphenylaldehyde, to prepare 170 mg the compound. 1H-NMR (400 MHz, DMSO-d6) δ0.90-0.94 (m, 6H); δ1.25-1.39 (m, 4H); δ1.63-2.13 (m, 8H); δ4.12-4.13 (d, 1H); δ5.49-5.50 (m, 1H); δ6.48-6.52 (m, 1H); δ7.38-7.40 (m, 3H); δ7.52-7.54 (m, 2H); δ7.66-7.70 (d, 1H). MS(TOF) 373.6 (M+).

Example 55 N-[1-(3-cyclohexyl thioureido)-2-methylpropyl] cinnamamide

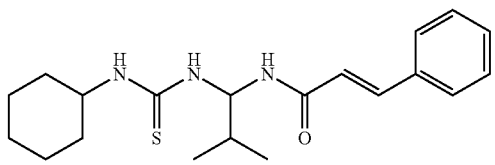 [SMILES: CC(C)C(NC(=O)/C=C/c1ccccc1)NC(=S)NC1CCCCC1]

The method of Example 24 was used, except that cyclohexylamine was used in place of aniline, isobutyraldehyde was used in place of isovaleraldehyde, phenylaldehyde was used in place of 3,4,5-trimethoxy phenylaldehyde, to prepare 170 mg the compound ( ). 1H-NMR (400 MHz, DMSO-d6) δ0.87-0.92 (m, 6H); δ1.10-1.29 (m, 6H); δ1.56-1.87 (m, 5H); δ2.12 (s, 1H); δ3.98 (s, 1H); δ6.68-6.72 (d, 1H); 7.39-7.44 (q, 4H); δ7.57-7.66 (d, 2H). MS(TOF) 359.6 (M+).

Example 56 N-[1-(3-cyclohexyl thioureido)-2,2-dimethylpropyl] cinnamamide

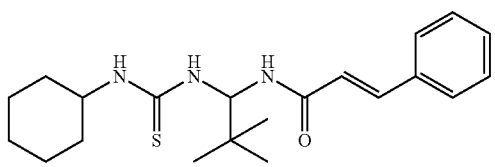 [SMILES: CC(C)(C)C(NC(=O)/C=C/c1ccccc1)NC(=S)NC1CCCCC1]

The method of Example 24 was used, except that cyclohexylamine was used in place of aniline, pivaldehyde was used in place of isovaleraldehyde, phenylaldehyde was used in place of 3,4,5-trimethoxyphenylaldehyde, to prepare 170 mg the compound. 1H-NMR (400 MHz, DMSO-d6) δ0.98-1.35 (m, 14H); δ1.57-2.10 (m, 5H); δ4.10-4.12 (d, 1H); δ5.19-5.24 (m, 1H); δ5.61 (s, 1H); δ6.03-6.05 (s, 1H); δ6.47-6.59 (d, 1H); δ7.35-7.38 (t, 2H); δ7.50-7.54 (d, 2H); δ7.65-7.70 (d, 2H). MS(TOF) 373.6 (M+).

Example 57 the Effect of the Compounds of the Invention on Reversing Drug Resistance in Tumors 1. Experimental Materials Cells: (BT474 and SK-BR3 are Lapatinib-sensitive human breast cancer cell strains; BT/LapR and SK/LapR are secondary Lapatinib-resistant human breast cancer cell strains upon Lapatinib stimulation; MDA-MB-361 and MDA-MB-453 are natural Lapatinib-resistant human breast cancer cell strains. BT474, MDA-MB-361, SK-BR3 and MDA-MB-453 are from American Type Culture Collection (ATCC))

| Name | Generation | Survival rate % |
|---|---|---|
| BT474 | P103 | 100 |
| BT/Lap$^R$1.0 | / | 97.12 |
| MDA-MB-361 | F72 | 97.76 |
| SK-BR3 | F28 | 95.95 |
| SK/Lap$^R$1.0 | / | 93.35 |
| MDA-MB-453 | F8 | 96.8 |

Lapatinib: 10 mM in DMSO, BioVision, Cat: 1624-100, Lot: 50324; ATPlit kit: CellTiter-Glo Substrate, Promega, Part: G755B, Lot: 32513501, EXP: 2014-05.

2. Experimental Procedure (1) Cell Plating

In a 100 mm culture dish full of adherent cells, digestion with 1 ml 0.25% pancreatin (GIBCO) was carried out at 37° C. for 5 min, and the reaction was stopped with 2 ml medium (containing 10% FBS, GIBCO). The cells were dispersed and collected. After cell count, the cells were diluted to a concentration of $1 \times 10^5$ cells/ml, and were seeded to a 96-well plate at 50 μl/well, 5000 cell/well, 60 wells in total, PBS instead of cells was added to the wells of the outmost circle, and the incubation was carried out at 37° C. for 24 h for adherence.

(2) Addition of a Compound and Lapatinib

In said cell plate, a sample group, a combination group, and a control group are set, respectively.

For the sample group, samples to be tested were diluted with DMSO to a final concentration of 5 μM; to control wells, the medium containing the same concentration of solvent corresponding to the compound was added, the concentrations of the compounds were identical in each well, 5 wells in parallel were set for each concentration, 25 μL/well, and 25 μL medium was added to each well (for the combination group, 25 μL Lapatinib was added to reach a final concentration of 1 μM). The incubation was carried out at 37° C. for 72 h.

(3) Detection

To each well, 50 μL ATPlite kit substrate solution was added. The plate was under shaking for 3 min, and was then placed in dark for 10 min. The lysis supernatant was drawn at 100 μL/well, and placed in a luminescent plate. The incubated luminescent plate was placed in an iluminescence apparatus, and the iluminescent value was read.

Data Processing

Cell survival rate (%)=Experimental group RLU/control group RLU×100%

GraphPad software was used to analyze and process data.

Coefficient of drug interaction (CDI) is used to evaluate the interaction of two drugs, CDI is calculated in accordance with the following formula: CDI=AB/(A×B)×100%. The calculation is performed according to the number of live cells (luminescent value), if CDI<1, the two drugs have a synergistic effect; if CDI<0.7, the synergistic effect is very significant; if CDI=1, the effect of the two drugs in combination is the sum of the effects of the two drugs; if CDI>1, the two drugs have an antagonistic effect.

The tested coefficients of drug interaction (CDI) of the example compounds and Lapatinib are shown in Table 1.

TABLE 1

CDI of example compounds and Lapatinib

| Compound No. | Molecular weight | BT474 | BT/Lap$^R$1.0 | MDA-MB-361 | SK-BR3 | SK/Lap$^R$1.0 | MDA-MB-453 |
|---|---|---|---|---|---|---|---|
| Example 24 | 457.6 | 1.03 | 0.98 | 0.92 | 1.04 | 1 | 1.12 |
| Example 25 | 458.6 | 0.94 | 0.97 | 0.93 | 1.04 | 0.93 | 1.2 |
| Example 26 | 457.6 | 1.02 | 0.96 | 0.99 | 1.03 | 1.02 | 0.89 |
| Example 27 | 458.6 | 0.98 | 1.01 | 0.96 | 1 | 0.97 | 1.32 |
| Example 28 | 441.5 | 1.07 | 0.99 | 0.93 | 1.06 | 0.95 | 1.21 |
| Example 29 | 442.5 | 1.05 | 0.99 | 1 | 0.98 | 1.26 | 1.05 |
| Example 30 | 442.5 | 0.94 | 0.93 | 0.85 | 0.94 | 0.82 | 1.28 |
| Example 31 | 458.6 | 1.01 | 1.2 | 0.85 | 1 | 0.95 | 1.38 |
| Example 32 | 471.6 | 0.65 | 1.25 | 0.91 | 1.13 | 0.89 | 1.42 |
| Example 33 | 472.6 | 0.81 | 0.97 | 0.89 | 0.96 | 0.88 | 1.19 |
| Example 34 | 472.6 | 0.98 | 1 | 0.87 | 0.98 | 0.85 | 1.41 |
| Example 35 | 428.5 | 0.96 | 1.04 | 0.86 | 0.99 | 0.9 | 1.37 |
| Example 36 | 427.5 | 0.97 | 0.96 | 0.98 | 1.07 | 0.94 | 1.3 |
| Example 37 | 352.5 | 0.98 | 1.02 | 0.99 | 0.99 | 1.03 | 1.34 |
| Example 38 | 367.5 | 0.86 | 0.93 | 1 | 1.16 | 0.93 | 1.21 |
| Example 39 | 381.5 | 0.79 | 1.19 | 0.92 | 1.2 | 0.95 | 1.2 |
| Example 40 | 367.5 | 0.85 | 0.95 | 0.95 | 1.14 | 0.99 | 1.37 |
| Example 41 | 351.5 | 0.91 | 0.99 | 0.91 | 1.09 | 1.02 | 1.07 |
| Example 42 | 353.5 | 0.92 | 0.99 | 0.96 | 1.14 | 0.99 | 1.15 |
| Example 43 | 395.5 | 1.03 | 1 | 0.95 | 1 | 0.93 | 1.28 |

TABLE 1-continued

CDI of example compounds and Lapatinib

| Compound No. | Molecular weight | BT474 | BT/Lap$^R$1.0 | MDA-MB-361 | SK-BR3 | SK/Lap$^R$1.0 | MDA-MB-453 |
|---|---|---|---|---|---|---|---|
| Example 44 | 471.6 | 0.94 | 0.93 | 0.93 | 0.96 | 0.98 | 1.12 |
| Example 45 | 455.6 | 1.59 | 0.79 | 0.93 | 1.05 | 1.04 | 0.98 |
| Example 46 | 395.6 | 0.74 | 0.79 | 0.94 | 1.29 | 1.25 | 1.64 |
| Example 47 | 381.5 | 0.84 | 0.97 | 1.05 | 1.15 | 0.98 | 1.39 |
| Example 48 | 381.5 | 0.92 | 0.96 | 1.15 | 1.15 | 0.99 | 1.2 |
| Example 49 | 365.5 | 0.9 | 0.96 | 0.95 | 1.08 | 0.99 | 1.2 |
| Example 50 | 473.6 | 1.02 | 1.02 | 0.97 | 1.06 | 0.96 | 1.4 |
| Example 51 | 463.6 | 0.73 | 0.94 | 1.09 | 0.96 | 1.38 | 1.27 |
| Example 52 | 463.6 | 0.56 | 0.86 | 0.92 | 0.88 | 1.11 | 1.18 |
| Example 53 | 449.6 | 0.82 | 0.8 | 1.19 | 0.97 | 1.23 | 1.33 |
| Example 54 | 373.6 | 0.77 | 0.98 | 0.9 | 1.16 | 1.14 | 1.2 |
| Example 55 | 359.6 | 0.89 | 1.01 | 0.94 | 1.2 | 1.8 | 1.41 |
| Example 56 | 373.6 | 0.77 | 1.21 | 0.96 | 1.19 | 1 | 1.32 |

Example 58 Evaluation of the Inhibitory Effect of the Compounds of the Invention on Hsp70 ATPase Activity 1. Materials and Reagents (1) Protein: Humanized Hsp70, Hsp40, expressed by *E. coli*.

(2) Sample to be tested: 26 compound solids with different colors and states. Positive drugs AZ (CAS:1054543-47-3) and VER 155008 (CAS: 1134156-31-2) were synthesized in the laboratory.

(3) ATPase detection reagents: ATP, Malachite green, polyvinyl alcohol, ammonium molybdate tetrahydrate purchased from SIGMA Co., citrate sodium produced by Sinopharm Chemical Reagent Co., Ltd.

(4) ATPase Assay buffer:
0.017% Triton X-100;
100 mM Tris-HCl;
20 mM KCl;
6 mM MgCl2, pH 7.4.

(5) Experimental conditions: cell assay was performed in BSL-2 laboratory of Institute of Pharmacology & Toxicology of AMMS.

(6) Preparation of solutions used in ATPase Assay:
1) Malachite green staining solution:
① 0.081% w/v malachite green: 0.0081 g Malachite green (SIGMA M6880-25G) was dissolved in 10 ml ddH$_2$O;
② 5.7% w/v ammonium molybdate: 0.57 g ammonium molybdate tetrahydrate (SIGMA, V900224-100G) was dissolved in 6M HCl solution (5 ml ddH$_2$O+5 mL concentrated HCl);
③ polyvinyl alcohol (2.3% w/v): 2.3 g polyvinyl alcohol (SIGMA, V900501-100G) was dissolved in 10 mL ddH2O under heating;
④ ddH$_2$O;
⑤ solutions of ①, ②, ③, ④ were mixed at a ratio of 2:1:1:2, and then standing at room temperature for 2 h; when the color turned from dark brown into golden yellow, the mixture was filtered with 0.22 μM filtration membrane for immediate use, wherein the mixture is prepared immediately at the time of use;
2) 25 mM ATP (A2383-5G, SIGMA): 0.069 g ATP/5 mL ddH2O;
3) Materials and apparatus
NC film 0.22 μM, (Milipore);
Costar 96 well plate;
Molecular Device, M5;

2. Experimental methods (1) Experimental steps:
1) 13.08 μl DnaK (0.15 mg/mL, 2.14 μM), 1.96 μl DnaJ (1 mg/mL, 25 μM) were dissolved in 7.96 μl Assay Buffer (0.017% Triton X-100, 100 mM Tris-HCl, 20 mM KCl, and 6 mM MgCl$_2$, pH 7.4), and the resultant solution was added to each well of the 96 well plate;
2) to each well of the 96 well plate, 1 μL sample to be tested (5 mM) or DMSO (solvent) was added, and vortexed with a Vortex agitator for 10 min; and then standing at 37° C. for 30 min;
3) to each well, 1 μL 25 mM ATP was added, to trigger the enzymatic reaction; (in each well, the final reaction volume was 25 μL, the final concentration of DnaK was 1.12 μM, the final concentration of DnaJ was 1.96 μM, the final concentration of DMSO was 4%, the final concentration of Triton X-100 was 0.01%, the final concentration of ATP was 1 mM, and the final concentration of sample to be tested was 200 μM), the enzymatic reaction was carried out at 37° C. for 3 h;
4) 80 μL Malachite green staining solution was then added to each well, and was vortexed gently;
5) 10 μL of 34% citrate sodium was then added immediately, and vortexed gently, to stop the ATP hydrolysis not caused by ATPase;
6) the resultant mixture was mixed thoroughly at 37° C. for 15 min, and OD620 was measured.

(2) Data Analysis

The inhibitory rate of Hsp70 ATPase activity is calculated in accordance with the following formula:

Inhibitory rate (%)=(DMSO well OD−Experimental well OD)/(DMSO well OD−Blank well OD)×100

1) Experimental Results

Criteria for preliminary screening: during preliminary screening, an example compound is regarded as effective in inhibition as long as its inhibitory rate is above 20% for Hsp70 ATPase at 200 μM.

In preliminary screening, after incubation with AZ, VER155008 for 30 min, positive control drugs could effectively inhibit Hsp70 ATPase activity at a concentration of 200 μM, with an inhibitory rate of 53.13% and 38.18%, respectively, which were consistent with the data reported in documents, indicating that the experimental system was tenable.

Figure 2:
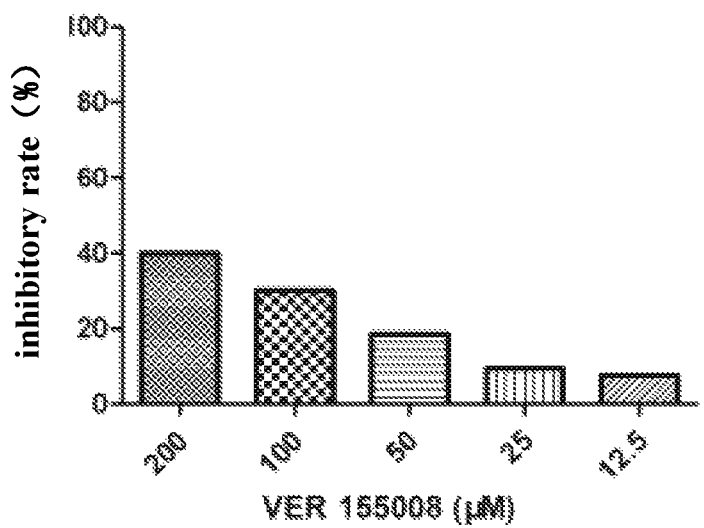
FIG. 2 illustrates the dose-response relationship with respect to the inhibition of Hsp70 ATPase activity by positive control drug VER155008.

In the first preliminary screening, AZ and VER155008 each were incubated with Hsp70/Hsp40, at a concentration of 200 μM, 100 μM, 50 μM, 25 μM, and 12.5 μM, respectively. They have a dose-response relationship with respect to inhibition of Hsp70 ATPase activity (as shown in FIGS. 1, 2), which further demonstrates the stability of the experimental system.

After the repeated screening was carried out twice, at a concentration of 200 μM, the example compounds, which were found to have an inhibitory rate of above 20% on Hsp70 ATPase activity, are shown in Table 2.

TABLE 2

Inhibitory rate of example compounds on activity of Hsp70 ATPase

| ID | Inhibitory rate (%) | Standard Deviation (SD) |
|---|---|---|
| AZ | 53.04 | 0.89 |
| VER155008 | 43.03 | 3.00 |
| Example 24 | 50.42 | 3.91 |
| Example 25 | 38.46 | 5.64 |
| Example 26 | 4.55 | 5.07 |
| Example 27 | 2.17 | 8.90 |
| Example 28 | 50.45 | 13.04 |
| Example 29 | 2.55 | 0.54 |
| Example 30 | −5.66 | 4.35 |
| Example 31 | 10.54 | 0.16 |
| Example 32 | 44.12 | 1.96 |
| Example 33 | 47.13 | 1.72 |
| Example 34 | 9.36 | 4.91 |
| Example 35 | −6.135 | 2.30 |
| Example 37 | 1.51 | 1.34 |
| Example 38 | 2.51 | 0.51 |
| Example 39 | 18.42 | 47.73 |
| Example 40 | 27.28 | 4.72 |
| Example 41 | 22.52 | 6.53 |
| Example 42 | −4.2 | 2.36 |
| Example 43 | 7.62 | 4.09 |
| Example 44 | 50.51 | 1.01 |
| Example 45 | 19.28 | 2.01 |
| Example 46 | 40.95 | 4.99 |
| Example 47 | 61.26 | 14.29 |
| Example 48 | −0.88 | 3.51 |
| Example 49 | 65.36 | 8.30 |
| Example 50 | 28.77 | 10.25 |
| Example 51 | 46.23 | 5.818 |
| Example 52 | 35.78 | 14.98 |
| Example 53 | 24.40 | 11.16 |
| Example 54 | 58.37 | 9.22 |
| Example 55 | 25.89 | 10.63 |
| Example 56 | 21.40 | 4.33 |

Although the embodiments of the invention have been described in detail, a person skilled in the art would understand that a variety of modifications and replacements may be conducted to the details according to all the teachings disclosed therein, these changes all fall into the protection scope of the invention. The scope of the invention is defined by the claims and any equivalent thereof.

What is claimed is:

1. A compound of Formula I:

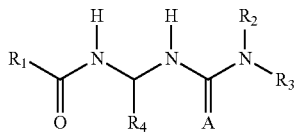

or a pharmaceutically acceptable salt or stereoisomer thereof, wherein:
A represents S;
$R_1$ represents —CH=CH-phenyl, wherein phenyl is optionally substituted with one or more groups selected from the group consisting of $C_{1-6}$alkyl, $C_{1-6}$alkoxy, cyano, halogen, hydroxy, amino, nitro, mono-$C_{1-6}$alkyl amino, di-$C_{1-6}$alkyl amino, $C_{2-6}$alkenyl, $C_{2-6}$alkynyl, $C_{1-6}$haloalkyl and $C_{1-6}$haloalkoxy;
$R_2$ represents hydrogen;
$R_3$ represents alkyl, cycloalkyl, alkoxyalkyl, aminoalkyl, aromatic heterocyclyl, arylalkyl, heterocyclylalkyl, aromatic heterocyclylalkyl, aryl or heterocyclyl, wherein $R_3$ is optionally substituted with one or more groups selected from the group consisting of $C_{1-6}$alkyl, $C_{1-6}$alkoxy, cyano, halogen, hydroxy, amino, nitro, mono-$C_{1-6}$alkyl amino, di-$C_{1-6}$alkyl amino, $C_{2-6}$alkenyl, $C_{2-6}$alkynyl, $C_{1-6}$haloalkyl and $C_{1-6}$haloalkoxy; and
$R_4$ represents alkyl or cycloalkyl.

2. The compound according to claim 1, or a pharmaceutically acceptable salt or stereoisomer thereof, wherein:
$R_3$ represents $C_{1-10}$alkyl, $C_{3-10}$cycloalkyl, $C_{1-6}$alkoxy-$C_{1-6}$alkyl, amino$C_{1-6}$alkyl, aromatic heterocyclyl, arylalkyl or aryl, wherein (i) the aromatic heterocyclyl is a monocyclic or bicyclic 5-10 membered aromatic ring system comprising at least one heteroatom independently selected from the group consisting of N, O and S, (ii) the aryl is selected from the group consisting of phenyl, naphthyl, 1,2,3,4-tetrahydronaphthyl and indenyl, and (iii) $R_3$ is optionally substituted with one or more groups selected from the group consisting of $C_{1-6}$alkyl, $C_{1-6}$alkoxy, cyano, halogen, hydroxy, amino, nitro, mono-$C_{1-6}$alkyl amino, di-$C_{1-6}$alkyl amino, $C_{2-6}$alkenyl, $C_{2-6}$alkynyl, $C_{1-6}$haloalkyl and $C_{1-6}$haloalkoxy; and
$R_4$ represents $C_{1-10}$ alkyl or $C_{3-8}$cycloalkyl.

3. The compound according to claim 1, or a pharmaceutically acceptable salt or stereoisomer thereof, wherein:
$R_3$ represents methyl, propyl, butyl, isobutyl, cyclohexyl, cycloheptyl, 2-methoxyethyl, 3-isopropoxypropyl, 2-N,N-dimethylethyl, 2-pyridyl, 3-pyridyl, 4-pyridyl, benzyl, 2-chlorobenzyl, phenyl, 2-methoxyphenyl, 4-methoxyphenyl, 4-fluorophenyl, 2-chlorophenyl, 4-chlorophenyl, 2-bromophenyl, 3-bromophenyl, 4-bromophenyl, 2-methylphenyl, 2,3-dimethylphenyl, 3-nitrophenyl, 2,4-difluorophenyl, 3-chloro-2-methylphenyl, 2,3-dichlorophenyl or 4-hydroxyphenyl; and
$R_4$ represents propyl, isopropyl, isobutyl, tert-butyl, tert-pentyl, neopentyl, neohexyl or cyclopropyl.

4. The compound according to claim 1, or a pharmaceutically acceptable salt or stereoisomer thereof, wherein:
$R_1$ represents —CH=CH-phenyl, wherein phenyl is optionally substituted at carbons 3, 4 and 5 with methoxy;
$R_3$ represents methyl, propyl, butyl, isobutyl, cyclohexyl, cycloheptyl, 2-methoxyethyl, 3-isopropoxypropyl, 2-N,N-dimethylethyl, 2-pyridyl, 3-pyridyl, 4-pyridyl, benzyl, 2-chlorobenzyl, phenyl, 2-methoxyphenyl, 4-methoxyphenyl, 4-fluorophenyl, 2-chlorophenyl, 4-chlorophenyl, 2-bromophenyl, 3-bromophenyl, 4-bromophenyl, 2-methylphenyl, 2,3-dimethylphenyl, 3-nitrophenyl, 2,4-difluorophenyl, 3-chloro-2-methylphenyl, 2,3-dichlorophenyl or 4-hydroxyphenyl; and
$R_4$ represents propyl, isopropyl, isobutyl, tert-butyl, tert-pentyl, neopentyl, neohexyl or cyclopropyl.

5. The compound according to claim 1, or a pharmaceutically acceptable salt or stereoisomer thereof, wherein the compound is selected from the group consisting of

(24) (2E)-N-[3-methyl-1-(3-phenyl thioureido) butyl]-3-(3,4,5-trimethoxyphenyl) acrylamide;
(25) (2E)-N-[3-methyl-1-(3-pyridinyl-3-yl thioureido) butyl]-3-(3,4,5-trimethoxyphenyl) acrylamide;
(26) (2E)-N-[2,2-dimethyl-1-(3-phenyl thioureido) propyl]-3-(3,4,5-trimethoxyphenyl) acrylamide;
(27) (2E)-N-[2,2-dimethyl-1-(3-pyridinyl-3-yl thioureido) propyl]-3-(3,4,5-trimethoxyphenyl) acrylamide;
(28) (2E)-N-[cyclopropyl-(3-phenyl thioureido)-methyl]-3-(3,4,5-trimethoxyphenyl) acrylamide;
(29) (2E)-N-[cyclopropyl-(3-pyridinyl-3-yl thioureido)-methyl]-3-(3,4,5-trimethoxyphenyl) acrylamide;
(30) (2E)-N-[cyclopropyl-(3-pyridinyl-2-yl thioureido)-methyl]-3-(3,4,5-trimethoxyphenyl) acrylamide;
(31) (2E)-N-[3-methyl-1-(3-pyridinyl-2-yl thioureido) butyl]-3-(3,4,5-trimethoxyphenyl) acrylamide;
(32) (2E)-N-[3,3-dimethyl-1-(3-phenyl thioureido) butyl]-3-(3,4,5-trimethoxyphenyl) acrylamide;
(33) (2E)-N-[3,3-dimethyl-1-(3-pyridinyl-3-yl thioureido) butyl]-3-(3,4,5-trimethoxyphenyl) acrylamide;
(34) (2E)-N-[3,3-dimethyl-1-(3-pyridinyl-2-yl thioureido) butyl]-3-(3,4,5-trimethoxyphenyl) acrylamide;
(35) (2E)-N-[2-methyl-1-(3-pyridinyl-2-yl thioureido) propyl]-3-(3,4,5-trimethoxyphenyl) acrylamide;
(36) (2E)-N-[2-methyl-1-(3-phenyl thioureido) propyl]-3-(3,4,5-trimethoxyphenyl) acrylamide;
(37) (2E)-N-[cyclopropyl-(3-pyridinyl-2-yl thioureido)-methyl] cinnamamide;
(38) (2E)-N-[3-methyl-1-(3-phenyl thioureido) butyl]cinnamamide;
(39) (2E)-N-[3,3-dimethyl-1-(3-phenyl thioureido) butyl] cinnamamide;
(40) (2E)-N-[2,2-dimethyl-1-(3-phenyl thioureido) propyl] cinnamamide;
(41) (2E)-N-[cyclopropyl-(3-phenyl thioureido)-methyl] cinnamamide;
(42) (2E)-N-[2-methyl-1-(3-phenyl thioureido) propyl] cinnamamide;
(43) (2E)-N-[3-methyl-1-(3-methyl thioureido) butyl]-3-(3,4,5-trimethoxyphenyl) acrylamide;
(44) (2E)-N-[2,2-dimethyl-1-(3-o-methyl phenyl thioureido) propyl]-3-(3,4,5-trimethoxyphenyl) acrylamide;
(45) (2E)-N-[cyclopropyl-(3-o-methyl phenyl thioureido)-methyl]-3-(3,4,5-trimethoxyphenyl) acrylamide;
(46) N-[3,3-dimethyl-1-(3-o-methyl phenyl thioureido) butyl] cinnamamide;
(47) N-[3-methyl-1-(3-o-methyl phenyl thioureido) butyl] cinnamamide;
(48) N-[2,2-dimethyl-1-(3-o-methyl phenyl thioureido) propyl] cinnamamide;
(49) N-[cyclopropyl-(3-o-methyl phenyl thioureido)-methyl] cinnamamide;
(50) (2E)-N-{1-[3-(4-methoxyphenyl) thioureido]-2-methylpropyl}-3-(3,4,5-trimethoxyphenyl) acrylamide;
(51) (2E)-N-[1-(3-cyclohexyl thioureido)-3-methylbutyl]-3-(3,4,5-trimethoxyphenyl) acrylamide;
(52) (2E)-N-[1-(3-cyclohexyl thioureido)-2,2-dimethylpropyl]-3-(3,4,5-trimethoxyphenyl) acrylamide;
(53) (2E)-N-[1-(3-cyclohexyl thioureido)-2-methylpropyl]-3-(3,4,5-trimethoxyphenyl) acrylamide;
(54) N-[1-(3-cyclohexyl thioureido)-3-methylbutyl]cinnamamide;
(55) N-[1-(3-cyclohexyl thioureido)-2-methylpropyl] cinnamamide; and
(56) N-[1-(3-cyclohexyl thioureido)-2,2-dimethylpropyl] cinnamamide.

6. A pharmaceutical composition comprising the compound according to claim 1, or a pharmaceutically acceptable salt or stereoisomer thereof, and a pharmaceutically acceptable carrier, excipient or diluent.

7. A method for inhibiting the expression of heat shock protein 70 in a cell, comprising contacting the cell with a therapeutically effective amount of the compound according to claim 1, or a pharmaceutically acceptable salt or stereoisomer thereof.

8. The method according to claim 7, wherein the method is performed in vitro or in vivo.

9. A method for combating drug resistance of a bacterium in a cell, comprising contacting the cell with a therapeutically effective amount of the compound according to claim 1, or a pharmaceutically acceptable salt or stereoisomer thereof.

10. The method according to claim 9, wherein the method is performed in vitro or in vivo.

11. A method for reversing drug resistance of a bacterium in a cell, comprising contacting the cell with a therapeutically effective amount of the compound according to claim 1, or a pharmaceutically acceptable salt or stereoisomer thereof.

12. The method according to claim 11, wherein the method is performed in vitro or in vivo.

13. A method for combating drug resistance of a tumor cell, comprising contacting the cell with a therapeutically effective amount of the compound according to claim 1, or a pharmaceutically acceptable salt or stereoisomer thereof.

14. The method according to claim 4, wherein the tumor cell is cancerous.

15. The method according to claim 14, wherein the cancer is selected from the group consisting of breast cancer, prostate cancer, liver cancer, esophageal cancer, stomach cancer and skin cancer.

16. The method according to claim 13, wherein the method is performed in vitro or in vivo.

17. A method for reversing drug resistance of a tumor cell, comprising contacting the cell with a therapeutically effective amount of the compound according to claim 1, or a pharmaceutically acceptable salt or stereoisomer thereof.

18. The method according to claim 17, wherein the tumor cell is cancerous.

19. The method according to claim 18, wherein the cancer is selected from the group consisting of breast cancer, prostate cancer, liver cancer, esophageal cancer, stomach cancer and skin cancer.

20. The method according to claim 17, wherein the method is performed in vitro or in vivo.

21. A method for treating a drug-resistant tumor in a subject, wherein the drug-resistance of the tumor is caused by a drug-resistant bacterium, comprising administering to a subject in need thereof a therapeutically effective amount of the compound according to claim 1, or a pharmaceutically acceptable salt or stereoisomer thereof.

22. The method according to claim 21, wherein the tumor is cancerous.

23. The method according to claim 22, wherein the cancer is selected from the group consisting of breast cancer, prostate cancer, liver cancer, esophageal cancer, stomach cancer and skin cancer.

24. A method for preparing a compound of Formula I according to claim 1:

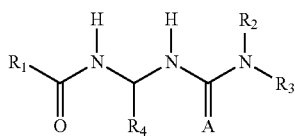

wherein:

A, $R_1$, $R_2$ and $R_3$ are as defined in claim 1; and $R_4$ represents alkyl;

the method comprising the following steps:

(i) reacting a compound of formula A:

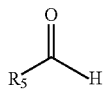

wherein $R_5$ represents phenyl, optionally substituted with one or more groups selected from the group consisting of $C_{1-6}$alkyl, $C_{1-6}$alkoxy, cyano, halogen, hydroxy, amino, nitro, mono-$C_{1-6}$alkyl amino, di-$C_{1-6}$alkyl amino, $C_{2-6}$alkenyl, $C_{2-6}$alkynyl, $C_{1-6}$haloalkyl and $C_{1-6}$haloalkoxy;

with malonic acid in pyridine at 80° C., to provide a compound of formula C:

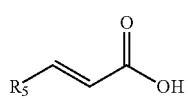

wherein $R_5$ represents phenyl, optionally substituted with one or more groups selected from the group consisting of $C_{1-6}$alkyl, $C_{1-6}$alkoxy, cyano, halogen, hydroxy, amino, nitro, mono-$C_{1-6}$alkyl amino, di-$C_{1-6}$alkyl amino, $C_{2-6}$alkenyl, $C_{2-6}$alkynyl, $C_{1-6}$haloalkyl and $C_{1-6}$haloalkoxy;

(ii) reacting the compound of formula C above with oxalyl chloride in the presence of dichloromethane, catalytic N,N-dimethylformamide and aqueous ammonia at 0° C., to provide a compound of formula F:

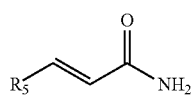

wherein $R_5$ represents phenyl, optionally substituted with one or more groups selected from the group consisting of $C_{1-6}$alkyl, $C_{1-6}$alkoxy, cyano, halogen, hydroxy, amino, nitro, mono-$C_{1-6}$alkyl amino, di-$C_{1-6}$alkyl amino, $C_{2-6}$alkenyl, $C_{2-6}$alkynyl, $C_{1-6}$haloalkyl and $C_{1-6}$haloalkoxy; or (iii) reacting the compound of formula F above with benzotriazole and a compound of formula:

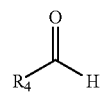

wherein $R_4$ represents alkyl;

to provide a compound of formula L:

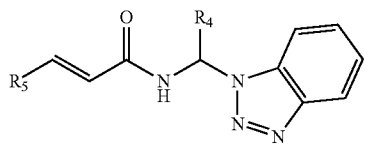

wherein:

$R_4$ represents alkyl; and $R_5$ represents phenyl, optionally substituted with one or more groups selected from the group consisting of $C_{1-6}$alkyl, $C_{1-6}$alkoxy, cyano, halogen, hydroxy, amino, nitro, mono-$C_{1-6}$alkyl amino, di-$C_{1-6}$alkyl amino, $C_{2-6}$alkenyl, $C_{2-6}$alkynyl, $C_{1-6}$haloalkyl and $C_{1-6}$haloalkoxy; and (iv) reacting the compound of formula L above with a compound of formula K:

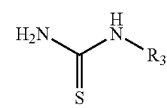

wherein $R_3$ represents alkyl, cycloalkyl, alkoxyalkyl, aminoalkyl, aromatic heterocyclyl, arylalkyl, heterocyclylalkyl, aromatic heterocyclylalkyl, aryl or heterocyclyl, wherein $R_3$ is optionally substituted with one or more groups selected from the group consisting of $C_{1-6}$alkyl, $C_{1-6}$alkoxy, cyano, halogen, hydroxy, amino, nitro, mono-$C_{1-6}$alkyl amino, di-$C_{1-6}$alkyl amino, $C_{2-6}$alkenyl, $C_{2-6}$alkynyl, $C_{1-6}$haloalkyl and $C_{1-6}$haloalkoxy;

in anhydrous tetrahydrofuran in the presence of sodium hydride, to provide a compound of Formula I:

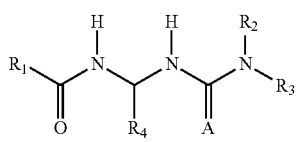

wherein:

$R_1$, $R_2$ and $R_3$ are as defined in claim 1; and $R_4$ represents alkyl.

25. A method for preparing a compound of Formula I according to claim 1:

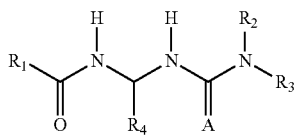

I wherein:

A, $R_1$, $R_2$ and $R_3$ are as defined in claim 1; and $R_4$ represents alkyl;

the method comprising the following steps:

(i) reacting a compound of formula A:

A wherein $R_5$ represents phenyl, optionally substituted with one or more groups selected from the group consisting of $C_{1-6}$alkyl, $C_{1-6}$alkoxy, cyano, halogen, hydroxy, amino, nitro, mono-$C_{1-6}$alkyl amino, di-$C_{1-6}$alkyl amino, $C_{2-6}$alkenyl, $C_{2-6}$alkynyl, $C_{1-16}$haloalkyl and $C_{1-6}$haloalkoxy;

with malonic acid in pyridine at 80° C., to provide a compound of formula C:

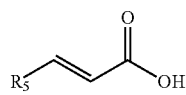

C wherein $R_5$ represents phenyl, optionally substituted with one or more groups selected from the group consisting of $C_{1-6}$alkyl, $C_{1-6}$alkoxy, cyano, halogen, hydroxy, amino, nitro, mono-$C_{1-6}$alkyl amino, di-$C_{1-6}$alkyl amino, $C_{2-6}$alkenyl, $C_{2-6}$alkynyl, $C_{1-6}$haloalkyl and $C_{1-6}$haloalkoxy;

(ii) reacting the compound of formula C above with p-toluenesulfonyl chloride in dichloromethane, to provide a compound of formula E:

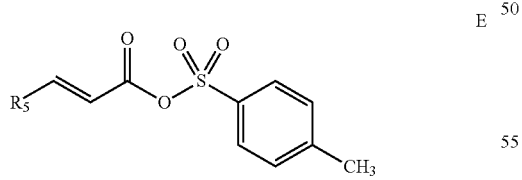

E wherein $R_5$ represents phenyl, optionally substituted with one or more groups selected from the group consisting of $C_{1-6}$alkyl, $C_6$alkoxy, cyano, halogen, hydroxy, amino, nitro, mono-$C_{1-6}$alkyl amino, di-$C_{1-6}$alkyl amino, $C_{2-6}$alkenyl, $C_{2-6}$alkynyl, $C_{1-6}$haloalkyl and $C_{1-6}$haloalkoxy;

(iii) reacting the compound of formula E above with aqueous ammonia under reflux, to provide a compound of formula F:

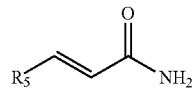

F wherein $R_5$ represents phenyl, optionally substituted with one or more groups selected from the group consisting of $C_{1-6}$alkyl, $C_6$alkoxy, cyano, halogen, hydroxy, amino, nitro, mono-$C_{1-6}$alkyl amino, di-$C_{1-6}$alkyl amino, $C_{2-6}$alkenyl, $C_{2-6}$alkynyl, $C_{1-6}$haloalkyl and $C_{1-6}$haloalkoxy; or (iv) reacting the compound of formula F above with benzotriazole and a compound of formula:

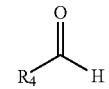

wherein $R_4$ represents alkyl;

to provide a compound of formula L:

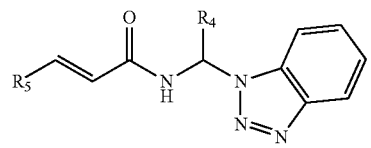

L wherein:

$R_4$ represents alkyl; and $R_5$ represents phenyl, optionally substituted with one or more groups selected from the group consisting of $C_{1-6}$alkyl, $C_{1-6}$alkoxy, cyano, halogen, hydroxy, amino, nitro, mono-$C_{1-6}$alkyl amino, di-$C_{1-6}$alkyl amino, $C_{2-6}$alkenyl, $C_{2-6}$alkynyl, $C_{1-6}$haloalkyl and $C_{1-6}$haloalkoxy; and (v) reacting the compound of formula L above with a compound of formula K:

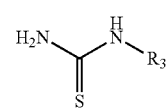

K wherein $R_3$ represents alkyl, cycloalkyl, alkoxyalkyl, aminoalkyl, aromatic heterocyclyl, arylalkyl, heterocyclylalkyl, aromatic heterocyclylalkyl, aryl or heterocyclyl, wherein $R_3$ is optionally substituted with one or more groups selected from the group consisting of $C_{1-6}$alkyl, $C_{1-6}$alkoxy, cyano, halogen, hydroxy, amino, nitro, mono-$C_{1-6}$alkyl amino, di-$C_{1-6}$alkyl amino, $C_{2-6}$alkenyl, $C_{2-6}$alkynyl, $C_{1-6}$haloalkyl and $C_{1-6}$haloalkoxy;

in anhydrous tetrahydrofuran in the presence of sodium hydride, to provide a compound of Formula I:

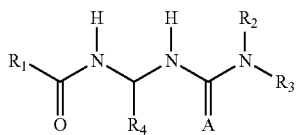
wherein:
$R_1$, $R_2$ and $R_3$ are as defined in claim 1; and
$R_4$ represents alkyl.
* * * * *